US010874581B2

(12) United States Patent
Shockley, Jr. et al.

(10) Patent No.: US 10,874,581 B2
(45) Date of Patent: Dec. 29, 2020

(54) METHOD OF CLEARING A BIOLOGICAL AIRWAY USING A SELF-CONTAINED PORTABLE POSITIONABLE OSCILLATING MOTOR ARRAY

(71) Applicant: INTERNATIONAL BIOPHYSICS CORPORATION, Austin, TX (US)

(72) Inventors: Harold David Shockley, Jr., Austin, TX (US); Geoffrey Albert Marcek, Austin, TX (US); Robert Wiley Ellis, Miramar, FL (US)

(73) Assignee: International Biophysics Corporation, Austin, TX (US)

( * ) Notice: Subject to any disclaimer, the term of this patent is extended or adjusted under 35 U.S.C. 154(b) by 125 days.

(21) Appl. No.: 14/876,479

(22) Filed: Oct. 6, 2015

(65) Prior Publication Data

US 2016/0095793 A1 Apr. 7, 2016

Related U.S. Application Data

(60) Provisional application No. 62/060,772, filed on Oct. 7, 2014, provisional application No. 62/101,131, filed
(Continued)

(51) Int. Cl.
*A61H 23/00* (2006.01)
*A61H 23/02* (2006.01)
(Continued)

(52) U.S. Cl.
CPC ............. *A61H 23/02* (2013.01); *A61B 5/055* (2013.01); *A61B 5/4833* (2013.01);
(Continued)

(58) Field of Classification Search
CPC .... A61H 23/00; A61H 23/02; A61H 23/0218; A61H 23/0236; A61H 23/0245;
(Continued)

(56) References Cited

U.S. PATENT DOCUMENTS

| | | | |
|---|---|---|---|
| 3,053,250 | A | 9/1962 | Stubbs |
| 3,310,050 | A | 3/1967 | Goldfarb |

(Continued)

FOREIGN PATENT DOCUMENTS

| | | |
|---|---|---|
| DE | 202008015893 | 7/2009 |
| WO | 2010/071919 | 7/2010 |

(Continued)

OTHER PUBLICATIONS

Tackell, M. W. et al., "Lung function improvement with AffloVest® HFCWO use: a clinician's perspective on PFT score data from 25 patients with cystic fibrosis." May 2016.

(Continued)

*Primary Examiner* — Michael J Tsai
(74) *Attorney, Agent, or Firm* — Kowert, Hood, Munyon, Rankin & Goetzel, P.C.; Gareth M. Sampson

(57) ABSTRACT

In some embodiments, a method may include clearing a biological airway. The method may include positioning an inner wearable harness on a torso of a subject. The method may include selectively positioning at least some of a plurality of engines on and/or adjacent at least one treatment area. At least one of the plurality of engines may be releasably couplable to the inner wearable harness. The method may include positioning an outer wearable harness on a torso of a subject. The method may include applying an oscillation force to at least one of the treatment areas using at least some of the plurality of engines. The method may include adjusting the applied oscillation force to the treatment area by activating the outer wearable harness. The method may include mobilizing at least some secretions in an airway within the subject substantially adjacent the at least one treatment area.

22 Claims, 21 Drawing Sheets

Related U.S. Application Data on Jan. 8, 2015, provisional application No. 62/183,819, filed on Jun. 24, 2015.

(51) Int. Cl.

| | |
|---|---|
| ***A61B 5/00*** | (2006.01) |
| ***A61H 1/00*** | (2006.01) |
| ***A61B 5/055*** | (2006.01) |
| ***A61H 31/00*** | (2006.01) |
| *A61H 11/02* | (2006.01) |
| *A61H 11/00* | (2006.01) |
| *A61B 90/00* | (2016.01) |

(52) U.S. Cl.

CPC .......... *A61B 5/4848* (2013.01); *A61B 5/6805* (2013.01); *A61H 1/006* (2013.01); *A61H 1/008* (2013.01); *A61H 23/004* (2013.01); *A61H 23/0218* (2013.01); *A61H 23/0236* (2013.01); *A61H 23/0254* (2013.01); *A61H 31/00* (2013.01); *A61B 5/6844* (2013.01); *A61B 2090/374* (2016.02); *A61B 2090/376* (2016.02); *A61H 11/02* (2013.01); *A61H 2011/005* (2013.01); *A61H 2201/0111* (2013.01); *A61H 2201/0157* (2013.01); *A61H 2201/0192* (2013.01); *A61H 2201/1207* (2013.01); *A61H 2201/165* (2013.01); *A61H 2201/1619* (2013.01); *A61H 2201/1652* (2013.01); *A61H 2201/50* (2013.01); *A61H 2201/501* (2013.01); *A61H 2201/5002* (2013.01); *A61H 2201/5038* (2013.01); *A61H 2201/5046* (2013.01); *A61H 2201/5058* (2013.01); *A61H 2201/5061* (2013.01); *A61H 2201/5071* (2013.01); *A61H 2201/5084* (2013.01); *A61H 2201/5097* (2013.01); *A61H 2205/08* (2013.01); *A61H 2205/084* (2013.01); *A61H 2230/405* (2013.01)

(58) Field of Classification Search

CPC ............ A61H 23/0254; A61H 23/0263; A61H 2023/002; A61H 23/04

See application file for complete search history.

(56) References Cited

U.S. PATENT DOCUMENTS 3,351,053 A 11/1967 Stuttle
3,612,046 A 10/1971 Gaylord
4,216,766 A 8/1980 Duykers et al.
4,257,408 A 3/1981 Ramey
4,979,502 A * 12/1990 Hunt ...................... A61H 23/02 601/15
5,235,967 A 8/1993 Arbisi et al.
5,273,028 A 12/1993 McLeod
5,363,863 A 11/1994 Lelli et al.
5,437,617 A 8/1995 Heinz et al.
5,884,338 A 3/1999 Golde
6,152,855 A 11/2000 Dean, Jr.
6,193,678 B1 * 2/2001 Brannon ............ A61H 23/0263 601/15
6,329,638 B1 * 12/2001 Bloodworth ........... A61H 23/02 219/211
6,471,663 B1 10/2002 Van Brunt et al.
6,514,200 B1 2/2003 Khouri
6,926,667 B2 8/2005 Khouri
6,962,277 B2 11/2005 Quintana et al.
7,147,610 B2 * 12/2006 Maalouf ................ A61H 23/02 601/15
7,207,953 B1 4/2007 Goicaj
7,374,550 B2 5/2008 Hansen et al.
7,890,342 B1 2/2011 Yruko et al.
7,954,900 B2 6/2011 Shantha et al.
8,332,236 B2 12/2012 Yurko et al.
8,460,223 B2 6/2013 Huster et al.
8,786,999 B2 7/2014 Locke
8,870,796 B2 10/2014 Hoffmann
8,950,207 B2 2/2015 Ranes et al.
9,289,350 B2 3/2016 Helgeson et al.
9,549,869 B2 1/2017 DeVlieger et al.
9,839,553 B2 12/2017 Bannister
9,895,287 B2 2/2018 Shockley et al.
9,907,488 B2 3/2018 Barduson
9,907,725 B2 3/2018 Shockley et al.
9,956,134 B2 5/2018 Shockley et al.
9,968,511 B2 5/2018 Huster et al.
10,034,813 B1 7/2018 Silver
10,039,692 B2 8/2018 Nickelson
10,159,623 B2 12/2018 Leftly
10,251,810 B2 4/2019 Shockley et al.
2002/0013516 A1 1/2002 Freyre et al.
2003/0028132 A1 * 2/2003 Bastia ................ A61H 23/0254 601/57
2003/0199899 A1 10/2003 Boecker
2004/0039317 A1 2/2004 Souney et al.
2004/0082237 A1 4/2004 Farmer et al.
2004/0133133 A1 7/2004 Dreimann et al.
2004/0158177 A1 8/2004 Van Brunt et al.
2005/0054958 A1 * 3/2005 Hoffmann ............ A61B 17/225 601/46
2005/0126578 A1 6/2005 Garrison et al.
2005/0234372 A1 10/2005 Hansen et al.
2005/0235988 A1 10/2005 Hansen et al.
2006/0009684 A1 1/2006 Kim
2006/0015045 A1 1/2006 Zets et al.
2006/0047230 A1 * 3/2006 Talish .................... A61H 23/02 601/46
2006/0075537 A1 4/2006 Tsai
2006/0218692 A1 * 10/2006 Lamarque .......... A41D 13/1245 2/114
2007/0197881 A1 8/2007 Wolf et al.
2007/0239087 A1 10/2007 Kivisto
2008/0000477 A1 1/2008 Huster et al.
2008/0027363 A1 * 1/2008 Brueckmann ...... A61H 23/0263 601/70
2008/0086062 A1 4/2008 Hansen et al.
2008/0108914 A1 * 5/2008 Brouqueyre ......... A61H 9/0078 601/2
2008/0275343 A1 11/2008 Hoffmann
2009/0069728 A1 3/2009 Hoffman et al.
2009/0177222 A1 7/2009 Brown et al.
2009/0234256 A1 9/2009 Helgeson et al.
2009/0255022 A1 10/2009 Smith et al.
2010/0071919 A1 3/2010 Muzzy et al.
2010/0113993 A1 5/2010 Davis et al.
2010/0292568 A1 11/2010 Droitcour et al.
2011/0139836 A1 6/2011 Klann
2011/0162121 A1 7/2011 Klann
2011/0166486 A1 7/2011 Kumanomido
2012/0022415 A1 1/2012 Mullen et al.
2012/0185999 A1 7/2012 Raviv
2012/0186000 A1 7/2012 Raviv
2012/0259255 A1 10/2012 Tomlinson et al.
2012/0291798 A1 11/2012 Park et al.
2013/0037531 A1 2/2013 Gray et al.
2013/0211294 A1 * 8/2013 Bohris ................. A61H 23/008 601/4
2013/0261518 A1 10/2013 Hansen et al.
2013/0289455 A1 10/2013 Clapp et al.
2013/0289456 A1 10/2013 Cang Guo et al.
2014/0005579 A1 1/2014 Drlik et al.
2014/0012167 A1 1/2014 DeVlieger et al.
2014/0150791 A1 6/2014 Birnkrant et al.
2014/0257151 A1 9/2014 Chikkanaravangala et al.
2014/0257153 A1 * 9/2014 Nickelson .......... A61H 23/0263 601/150
2014/0358189 A1 12/2014 Mashiach et al.
2015/0265209 A1 9/2015 Zhang
2015/0272236 A1 10/2015 Chen et al.
2015/0272805 A1 10/2015 Burnett et al.

(56) References Cited

U.S. PATENT DOCUMENTS

| | | | |
|---|---|---|---|
| 2015/0305974 | A1 | 10/2015 | Ehrenreich et al. |
| 2015/0374578 | A1 | 12/2015 | Matsuura |
| 2016/0089571 | A1 | 3/2016 | Wesley et al. |
| 2016/0095782 | A1 | 4/2016 | Shockley et al. |
| 2016/0095783 | A1 | 4/2016 | Shockley et al. |
| 2016/0095791 | A1 | 4/2016 | Shockley et al. |
| 2016/0095792 | A1 | 4/2016 | Shockley et al. |
| 2016/0095793 | A1 | 4/2016 | Shockley et al. |
| 2016/0095790 | A1 | 6/2016 | Shockley et al. |
| 2016/0306932 | A1 | 10/2016 | Fateh et al. |
| 2017/0000686 | A1 | 1/2017 | Shockley et al. |
| 2017/0000687 | A1 | 1/2017 | Shockley et al. |
| 2017/0015697 | A1 | 1/2017 | Orum et al. |
| 2017/0095400 | A1 | 4/2017 | Shockley et al. |
| 2017/0177818 | A1 | 6/2017 | Eustis |
| 2018/0092801 | A1 | 4/2018 | Shockley et al. |
| 2019/0038502 | A1 | 2/2019 | Shockley et al. |

FOREIGN PATENT DOCUMENTS

| | | |
|---|---|---|
| WO | 2011/094883 | 8/2011 |
| WO | 2013/052817 | 4/2013 |
| WO | 2016057527 | 4/2016 |
| WO | 2018/093993 | 5/2018 |

OTHER PUBLICATIONS

AffloVest, International Biophysics Press Release, PRNewswire, May 11, 2016.

International Search Report and Written Opinion for PCT/US15/54261 dated Jan. 7, 2016. pp. 20.

International Biophysics Corporation AffloVest White Paper, "AffloVest Answering Needs: The Role of the AffloVest in the Respiratory Market", Oct. 2013.

The VibraVest by OxyCare GMbH product brochure. May, 2012.

Cooper, M. "An evidence-based study of adolescents with cystic fibrosis demonstrated that AffloVest® by International Biophysics contributed to improved lung function scores" Chicago, Illinois. Apr. 6, 2015.

International Biophysics Corporation "Clinical Study of the AffloVest as a High Frequency Chest Wall Oscillation Device" Mar. 2013.

International Biophysics Corporation AffloVest Pamphlet. Oct. 2013.

Co-Pending U.S. Appl. No. 14/876,472 entitled, "Self-Contained Portable Positionable Oscillating Motor Array" to Shockley et al. filed Oct. 6, 2015.

Co-Pending U.S. Appl. No. 14/876,476 entitled, "Method of Clearing a Biological Airway Using a Self-Contained Portable Positionable Oscillating Motor Array" to Shockley et al. filed Oct. 6, 2015.

Co-Pending U.S. Appl. No. 14/876,487 entitled, "Kit for Clearing a Biological Airway Including a Self-Contained Portable Positionable Oscillating Motor Array" to Shockley et al. filed Oct. 6, 2015.

Co-Pending U.S. Appl. No. 14/876,494 entitled, "Flexible Vest Including a Positionable Oscillating Motor Array" to Shockley et al. filed Oct. 6, 2015.

Co-Pending U.S. Appl. No. 14/876,504 entitled, "Self-Contained Portable Positionable Oscillating Motor Array Including Disposable and/or Recyclable Portions" to Shockley et al. filed Oct. 6, 2015.

Co-Pending U.S. Appl. No. 14/876,507 entitled, "Self-Contained Portable Positionable Oscillating Motor Array Including an Outer Harness Providing a Compressive Force" to Shockley et al. filed Oct. 6, 2015.

Non Final Office Action for U.S. Appl. No. 14/876,487 dated Apr. 6, 2018.

Non Final Office Action for U.S. Appl. No. 14/876,507 dated Apr. 6, 2018.

Co-Pending U.S. Appl. No. 15/728,887 entitled, "Systems and Methods for Monitoring a Subject's Effective Use of a Self-Contained Portable Positionable Oscillating Motor Array" to Shockley et al. filed Oct. 10, 2017.

NPL10_Hill-Rom MONARCH TM Airway Clearance System Pamphlet "Take More Control of Your Life" Apr. 13, 2017.

NPL09_International Preliminary Report on Patentability for PCT/US2015/054261 dated Apr. 11, 2017. pp. 18.

Non Final Office Action for U.S. Appl. No. 14/876,479 dated Oct. 5, 2017.

Non Final Office Action for U.S. Appl. No. 15/266,465 dated Dec. 20, 2016.

Final Office Action for U.S. Appl. No. 15/266,465 dated Jul. 3, 2017.

Non Final Office Action for U.S. Appl. No. 15/266,496 dated Dec. 2, 2016.

Final Office Action for U.S. Appl. No. 15/266,496 dated Jun. 14, 2017.

Non Final Office Action for U.S. Appl. No. 15/266,521 dated Dec. 29, 2016.

Final Office Action for U.S. Appl. No. 15/266,521 dated Jun. 30, 2017.

Non Final Office Action for U.S. Appl. No. 14/876,472 dated Dec. 15, 2017.

Notice of Allowance for U.S. Appl. No. 15/266,465 dated Oct. 30, 2017.

Notice of Allowance for U.S. App. No. 15/266,496 dated Dec. 21, 2017.

Notice of Allowance for U.S. Appl. No. 15/266,521 dated Sep. 26, 2017.

Non Final Office Action for U.S. Appl. No. 15/728,887 dated Feb. 28, 2018.

NPL11_International Search Report and Written Opinion for PCT/US17/61935 dated Feb. 6, 2018. pp. 12.

Notice of Allowance for U.S. Appl. No. 14/876,507 dated Jul. 23, 2018.

Final Office Action for U.S. Appl. No. 14/876,479 dated Jun. 13, 2018.

Final Office Action for U.S. Appl. No. 14/876,472 dated Jun. 14, 2018.

Advisory Action for U.S. Appl. No. 14/876,472 dated Aug. 24, 2018.

Non Final Office Action for U.S. Appl. No. 14/876,472 dated Oct. 9, 2018.

Advisory Action for U.S. Appl. No. 14/876,479 dated Aug. 24, 2018.

Non Final Office Action for U.S. Appl. No. 14/876,479 dated Nov. 1, 2018.

Final Office Action for U.S. Appl. No. 14/876,487 dated Sep. 6, 2018.

Non Final Office Action for U.S. Appl. No. 14/876,494 dated Oct. 4, 2018.

Final Office Action for U.S. Appl. No. 15/728,887 dated Sep. 6, 2018.

Non Final Office Action for U.S. Appl. No. 14/876,487 dated Jan. 2, 2019.

Notice of Allowance for U.S. Appl. No. 14/876,507 dated Nov. 27, 2018.

Advisory Action for U.S. Appl. No. 15/728,887 dated Nov. 28, 2018.

Non Final Office Action for U.S. Appl. No. 15/728,887 dated Jan. 7, 2019.

Non Final Office Action for U.S. Appl. No. 16/157,631 dated Jan. 2, 2019.

Final Office Action for U.S. Appl. No. 14/876,472 dated Mar. 27, 2019.

Final Office Action for U.S. Appl. No. 14/876,479 dated Apr. 12, 2019.

Final Office Action for U.S. Appl. No. 14/876,487 dated Jul. 29, 2019.

Final Office Action for U.S. Appl. No. 14/876,494 dated Apr. 11, 2019.

Final Office Action for U.S. Appl. No. 14/876,504 dated Mar. 28, 2019.

Final Office Action for U.S. Appl. No. 15/728,887 dated Jun. 13, 2019.

(56) References Cited

OTHER PUBLICATIONS

Final Office Action for U.S. Appl. No. 16/157,631 dated Jul. 1, 2019.
NPL12_Extended European Search Report for European Application No. 15848394.1-1126 dated May 11, 2018.
Co-Pending U.S. Appl. No. 15/266,465 entitled, "Self-Contained Portable Positionable Oscillating Motor Array System" to Shockley et al. filed Sep. 15, 2016.
Co-Pending U.S. Appl. No. 15/266,496 entitled, "Method of Clearing a Biological Airway Using a Self-Contained Portable Positionable Oscillating Motor Array" to Shockley et al. filed Sep. 15, 2016.
Co-Pending U.S. Appl. No. 15/266,521 entitled, "Kit for Clearing a Biological Airway Including a Self-Contained Portable Positionable Oscillating Motor Array" to Shockley et al. filed Sep. 15, 2016.
Co-Pending U.S. Appl. No. 15/353,383 entitled, :Systems and Methods for Monitoring a Subject's Effective Use of a Self-Contained Portable Positionable Oscillating Motor Array to Shockley et al. filed Nov. 16, 2016.
Non Final Office Action for U.S. Appl. No. 14/876,472 dated Sep. 30, 2019.
Final Office Action for U.S. Appl. No. 14/876,472 dated Mar. 12, 2020.
International Search Report and Written Opinion for PCT/US2019/055183 dated Dec. 5, 2019; 11 pages.
Advisory Action for U.S. Appl. No. 14/876,487 dated Oct. 9, 2019.
Non Final Office Action for U.S. Appl. No. 14/876,487 dated Feb. 5, 2020.
Advisory Action for U.S. Appl. No. 14/876,494 dated Jul. 1, 2019.
Non Final Office Action for U.S. Appl. No. 14/876,494 dated Sep. 20, 2019.
Final Office Action for U.S. Appl. No. 14/876,494 dated Feb. 21, 2020.
Final Office Action for U.S. Appl. No. 14/876,504 dated Sep. 17, 2019.
Advisory Action for U.S. Appl. No. 14/876,504 dated Dec. 4, 2019.
Non-Final Office Action for U.S. Appl. No. 14/876,504 dated Jan. 8, 2020.
Non-Final Office Action for U.S. Appl. No. 15/353,383 dated Feb. 24, 2020.
Office Action for Australian Application No. 2015328220 dated Jul. 1, 2019.
Office Action for European Application No. 15848394.1-1126 dated Apr. 21, 2020.
Non Final Office Action for U.S. Appl. No. 15/728,887 dated Oct. 1, 2019.
Notice of Allowance for U.S. Appl. No. 15/728,887 dated Feb. 11, 2020.
International Preliminary Report on Patentability for PCT/US17/61935 dated Feb. 14, 2019.
Supplemental Search Report for European Application No. 17872163.5 dated May 8, 2020.
Advisory Action for U.S. Appl. No. 16/157,631 dated Nov. 21, 2019.
Notice of Allowance for U.S. Appl. No. 16/157,631 dated May 14, 2020.
Co-Pending U.S. Appl. No. 16/157,631 entitled: "Systems and Methods for Effective Reuse of a Self-Contained Portable Positionable Oscillating Motor Array" to Shockley et al. filed Oct. 11, 2018.

* cited by examiner

FIG. 22
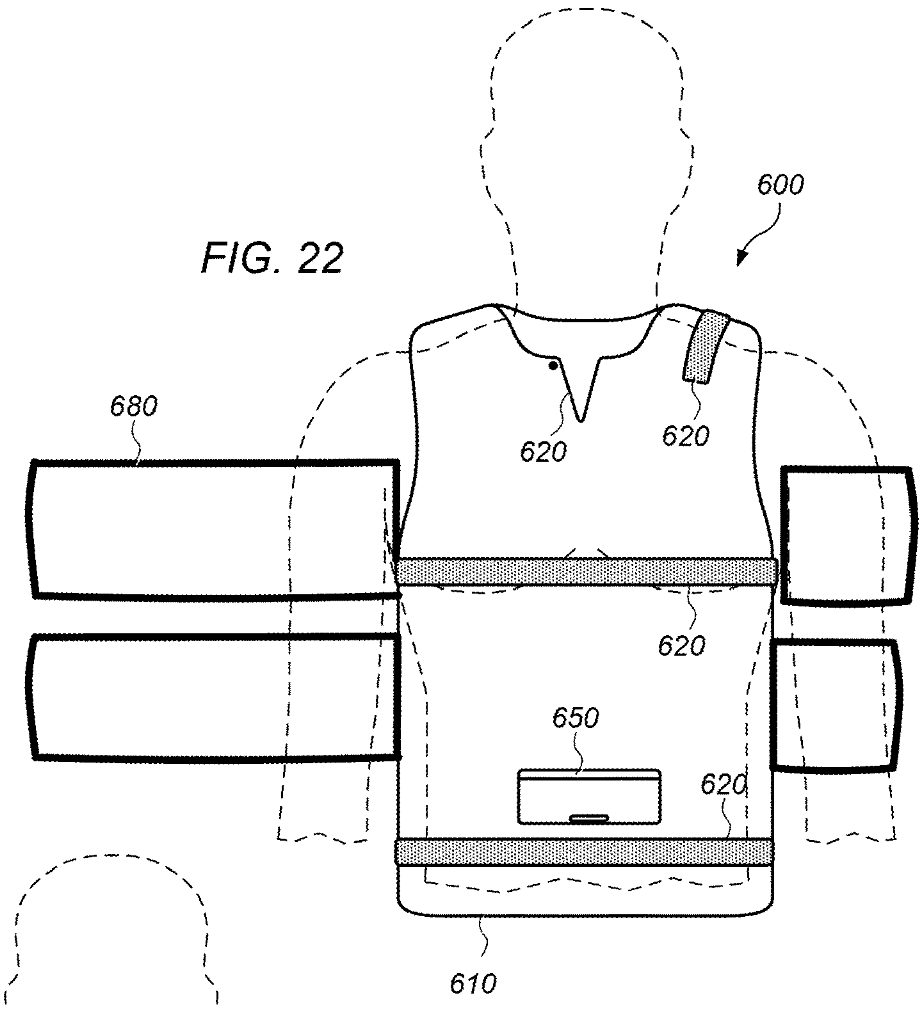
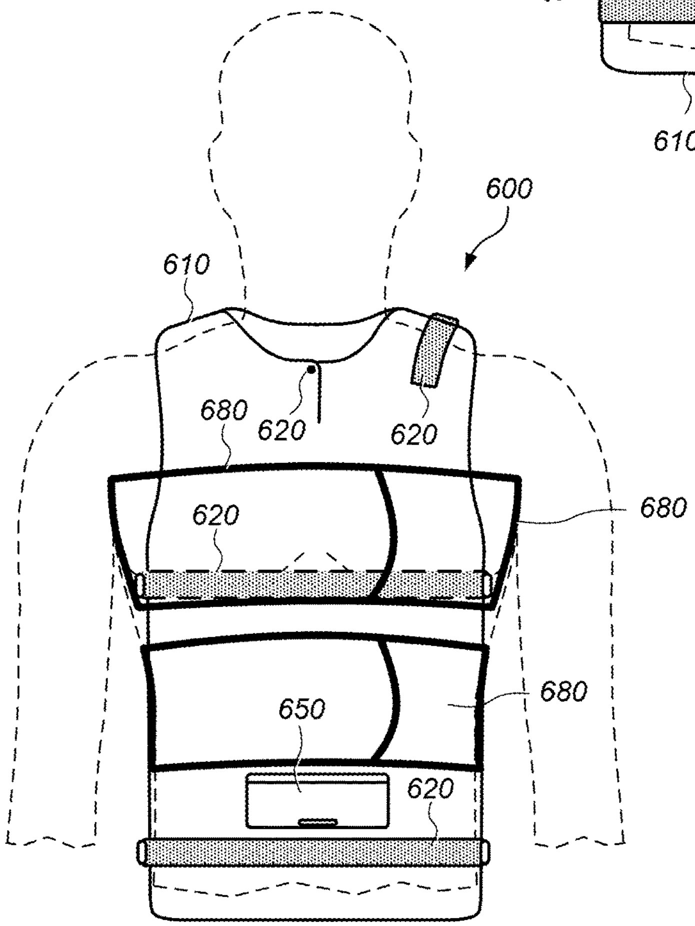
FIG. 23

METHOD OF CLEARING A BIOLOGICAL AIRWAY USING A SELF-CONTAINED PORTABLE POSITIONABLE OSCILLATING MOTOR ARRAY

PRIORITY CLAIM

This application is a claims priority to U.S. Provisional Patent Application No. 62/060,772 entitled "CHEST WALL OSCILLATION VEST" filed on Oct. 7, 2014, U.S. Provisional Patent Application No. 62/101,131 entitled "SELF-CONTAINED PORTABLE HIGH FREQUENCY PHYSIOLOGICAL OSCILLATOR" filed on Jan. 8, 2015, and U.S. Provisional Patent Application No. 62/183,819 entitled "SELF-CONTAINED PORTABLE POSITIONABLE OSCILLATING MOTOR ARRAY" filed on Jun. 24, 2015, all of which are incorporated by reference herein.

BACKGROUND OF THE INVENTION

1. Field of the Invention

The present disclosure generally relates to respiratory therapies. More particularly, the disclosure generally relates to a method and system for high frequency upper chest wall oscillation therapy.

2. Description of the Relevant Art

Subjects who are unable to mobilize their own lung secretions without assistance (subjects with, for example, chronic obstructive pulmonary disease (COPD)) are exceedingly common, which together account for over 1 million hospitalizations each year in the United States alone. Beta agonists, anti-cholinergics, and corticosteroids delivered in aerosolized forms are recommended in the treatment of COPD. These medications rely on deposition into distal airspaces to suppress airway inflammation or promote bronchodilation. Excessive mucous production and impaired airway mucociliary clearance can lead to airway plugging, and thereby reduce the deposition of and response to aerosolized medications. These considerations highlight the need for therapies that clear airways of mucus in the acute management of diseases such as cystic fibrosis, bronchiectasis (and other severe form of COPD), and certain neuromuscular diseases.

Manual percussion techniques of chest physiotherapy have been used for a variety of diseases, such as cystic fibrosis, emphysema, and chronic bronchitis, to remove excess mucus that collects in the lungs. To bypass dependency on a caregiver to provide this therapy, chest compression and oscillation devices have been developed to produce High Frequency Chest Wall Oscillation (HFCWO), a very successful method of airway clearance. High frequency chest wall oscillation (HFCWO) creates high velocity, low amplitude oscillation energy when applied through a vest worn over the thorax, and is used for airway mucus clearance in patients with cystic fibrosis, bronchiectasis, and neuromuscular disorders. Studies in patients with cystic fibrosis suggest that HFCWO applied via a vest is as effective as other modes of airway mucus clearance, including hand-held devices (e.g., flutter devices) and conventional chest physiotherapy. HFCWO offers the advantage that it can be performed in acutely ill patients who may be unable to use hand-held devices effectively, such as early in the course of hospitalization. Moreover, HFCWO can be performed without the assistance from trained health care personnel, and may therefore offer a practical advantage compared to chest physiotherapy.

Professional healthcare environments are required to constantly be vigilant regarding sanitation and cross contamination between patients. To this end medical equipment must be sanitized before being used again. However, sanitizing equipment is typically time consuming and/or expensive. As such much of the equipment used in healthcare environments which comes into direct contact with subjects is disposable (or covered by disposable sheaths). It is typically much easier and/or less expensive to throw away equipment which comes into contact with subjects as opposed to cleaning the equipment.

As such, it may advantageous to form a wearable HFCWO system with one or more disposable portions.

SUMMARY

In some embodiments, a system and/or method may include an inner wearable harness worn, during use, on a torso of a subject. The system may include a plurality of engines which when activated apply an oscillation force to at least one treatment area of the subject. At least some of the plurality of engines may be releasably couplable to the inner wearable harness. The system may include a positioning system which allows positioning at least one of the plurality of engines such that the oscillation force is applied to at least one of the treatment areas of the subject. The oscillation force may mobilize, during use, at least some secretions in an airway within the subject substantially adjacent the treatment area. The system may include an outer harness worn, during use, on a torso of a subject. The outer wearable harness, when activated, adjusts the oscillation force applied by at least some of the activated plurality of engines to the treatment area.

BRIEF DESCRIPTION OF THE DRAWINGS

Advantages of the present invention may become apparent to those skilled in the art with the benefit of the following detailed description of the preferred embodiments and upon reference to the accompanying drawings.

FIG. 22 depicts a front view of a representation of an embodiment of a portable high frequency chest wall oscillator inner harness including secured fasteners as well as two inactivated outer harnesses positioned on a subject.

FIG. 23 depicts a front view of a representation of an embodiment of a portable high frequency chest wall oscillator inner harness including secured fasteners as well as two activated outer harnesses positioned on a subject.

Figure 1:
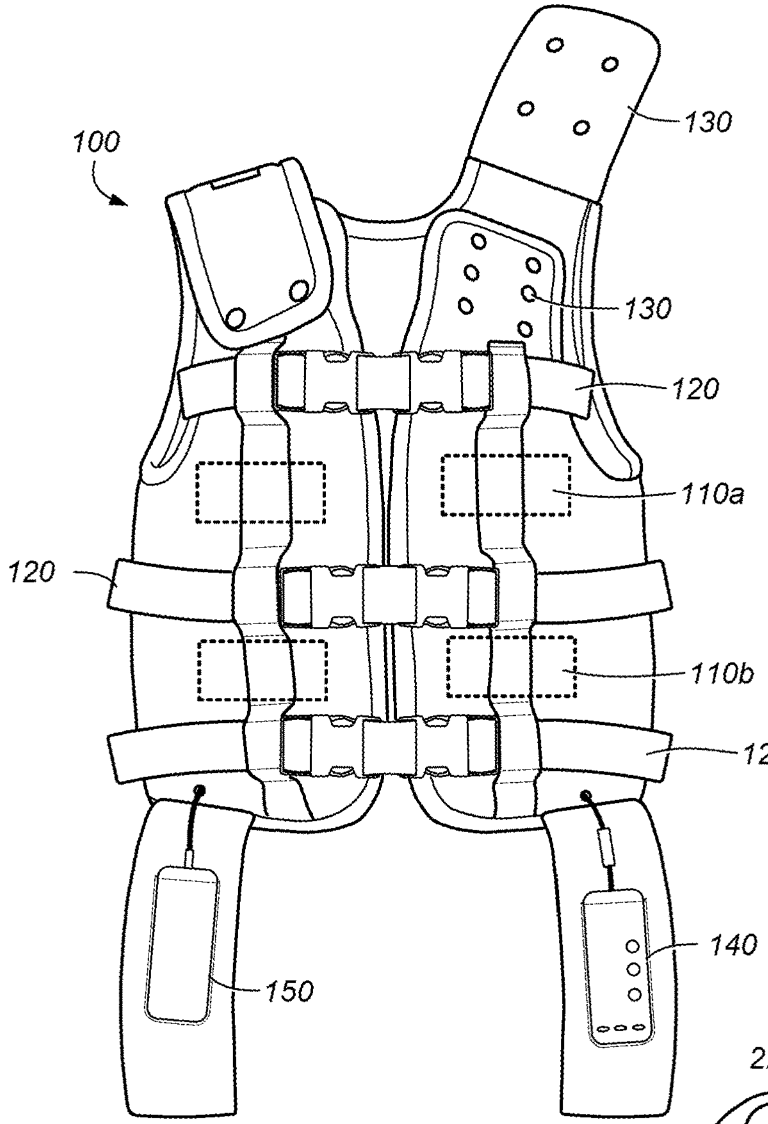
FIG. 1 depicts a front perspective view of a representation of an embodiment of a portable high frequency chest wall oscillator system.

While the invention is susceptible to various modifications and alternative forms, specific embodiments thereof are shown by way of example in the drawings and may herein be described in detail. The drawings may not be to scale. It should be understood, however, that the drawings and detailed description thereto are not intended to limit the invention to the particular form disclosed, but on the contrary, the intention is to cover all modifications, equivalents and alternatives falling within the spirit and scope of the present invention as defined by the appended claims.

The headings used herein are for organizational purposes only and are not meant to be used to limit the scope of the description. As used throughout this application, the word "may" is used in a permissive sense (i.e., meaning having the potential to), rather than the mandatory sense (i.e., meaning must). The words "include," "including," and "includes" indicate open-ended relationships and therefore mean including, but not limited to. Similarly, the words "have," "having," and "has" also indicated open-ended relationships, and thus mean having, but not limited to. The terms "first," "second," "third," and so forth as used herein are used as labels for nouns that they precede, and do not imply any type of ordering (e.g., spatial, temporal, logical, etc.) unless such an ordering is otherwise explicitly indicated. For example, a "third die electrically connected to the module substrate" does not preclude scenarios in which a "fourth die electrically connected to the module substrate" is connected prior to the third die, unless otherwise specified. Similarly, a "second" feature does not require that a "first" feature be implemented prior to the "second" feature, unless otherwise specified.

Various components may be described as "configured to" perform a task or tasks. In such contexts, "configured to" is a broad recitation generally meaning "having structure that" performs the task or tasks during operation. As such, the component can be configured to perform the task even when the component is not currently performing that task (e.g., a set of electrical conductors may be configured to electrically connect a module to another module, even when the two modules are not connected). In some contexts, "configured to" may be a broad recitation of structure generally meaning "having circuitry that" performs the task or tasks during operation. As such, the component can be configured to perform the task even when the component is not currently on. In general, the circuitry that forms the structure corresponding to "configured to" may include hardware circuits.

Various components may be described as performing a task or tasks, for convenience in the description. Such descriptions should be interpreted as including the phrase "configured to." Reciting a component that is configured to perform one or more tasks is expressly intended not to invoke 35 U.S.C. § 112 paragraph (f), interpretation for that component.

The scope of the present disclosure includes any feature or combination of features disclosed herein (either explicitly or implicitly), or any generalization thereof, whether or not it mitigates any or all of the problems addressed herein. Accordingly, new claims may be formulated during prosecution of this application (or an application claiming priority thereto) to any such combination of features. In particular, with reference to the appended claims, features from dependent claims may be combined with those of the independent claims and features from respective independent claims may be combined in any appropriate manner and not merely in the specific combinations enumerated in the appended claims.

It is to be understood the present invention is not limited to particular devices or biological systems, which may, of course, vary. It is also to be understood that the terminology used herein is for the purpose of describing particular embodiments only, and is not intended to be limiting. As used in this specification and the appended claims, the singular forms “a”, “an”, and “the” include singular and plural referents unless the content clearly dictates otherwise. Thus, for example, reference to “a linker” includes one or more linkers.

DETAILED DESCRIPTION

Definitions

Unless defined otherwise, all technical and scientific terms used herein have the same meaning as commonly understood by one of ordinary skill in the art.

The term “compression” as used herein generally refers to the application of balanced inward (e.g., “pushing”) forces to different points on a material or structure.

The term “connected” as used herein generally refers to pieces which may be joined or linked together.

The term “coupled” as used herein generally refers to pieces which may be used operatively with each other, or joined or linked together, with or without one or more intervening members.

The term “directly” as used herein generally refers to one structure in physical contact with another structure, or, when used in reference to a procedure, means that one process effects another process or structure without the involvement of an intermediate step or component.

The term “engine” as used herein generally refers to a machine designed to convert one form of energy into mechanical energy (e.g., electric motors, sonic wave generators, etc.).

The phrase “oscillation force” as used herein generally refers to a vibrational force, or a vibrational wave effect or wave form.

The term “pressure” as used herein generally refers to a force applied substantially perpendicular to a surface of an object.

Portable High Frequency Physiological Oscillator

Chest physiotherapy with bronchial drainage is a known treatment for mobilization and removal of airway secretions in many types of respiratory dysfunction especially in chronic lung disease (e.g., cystic fibrosis, brochiectasis, bronchitis, primary ciliary dyskinesia syndrome). Chest physiotherapy has been demonstrated to be effective in maintaining pulmonary function and prevention or reduction of respiratory complications in patients with chronic respiratory diseases. In some embodiments, a system and/or method may include clearing a biological airway. Biological airways may include any portion of the respiratory system including, but not limited to, trachea, bronchi, bronchioles, and alveoli.

The method may include positioning a wearable system on a subject. The method may include adjusting the wearable system such that an oscillation force is applied to at least a first zone and to at least a second zone of the subject (e.g., and possibly more zones). In some embodiments, an oscillation force may include a vibrational force, or a vibrational wave effect or wave form.

Figure 2:
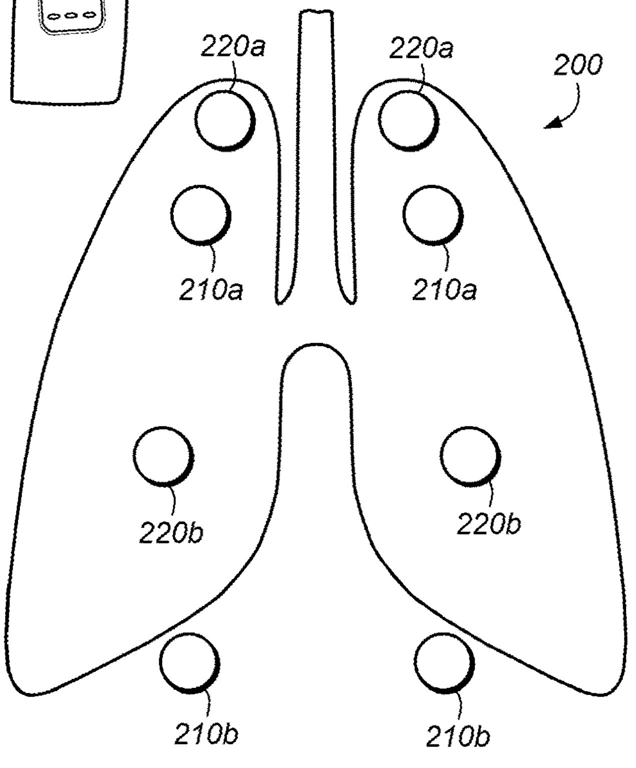
FIG. 2 depicts a front view of a representation of an embodiment of a pair of human lungs.

FIG. 1 depicts a front perspective view of a representation of an embodiment of a portable high frequency chest wall oscillator system 100. Known HFCWO systems do not allow for a user adjusting where forces are applied to on the subject. This is problematic because although some known HFCWO systems may come in different sizes to accommodate differently sized subjects, there are far too many people of different sizes and so it is impractical to produce enough differently sized systems for all of the differently sized subjects. FIG. 2 depicts a front view of a representation of an embodiment of a pair of human lungs 200. Known HFCWO systems may typically apply forces at zones 210*a-b*. A system 100 may allow for adjusting where forces are applied to the subject, for example, to what are identified as at least the first zone 220*a* and the second zone 220*b*. Applying high frequency forces to zones 220 as opposed to zones 210 may allow for greater remediation of symptoms associated with certain forms of chronic lung disease.

In some embodiments, the first zone 220*a* may be proximate to and below a collarbone of the subject (e.g., as depicted in FIG. 2). FIG. 2 depicts a front view of a representation of an embodiment of a pair of human lungs 200. In some embodiments, the second zone 220*b* may be positioned below first zone and proximate to and above a bottom of a rib cage of the subject (e.g., as depicted in FIG. 2). In some embodiments, the first and/or second zone may be positioned relative to any relevant markers (e.g., one or more of the subject’s physiological markers) which results in increased mobilization of secretions in an airway within the subject. The method may include applying a force (e.g., an oscillation force, a high frequency force, a pneumatic force, etc.) to the first zone and/or the second zone (e.g., and possibly additional zones) using a first engine 110*a* and a second engine 110*b* respectively. The method may include mobilizing secretions in an airway within the subject (e.g., substantially adjacent the first and/or second zone). In some embodiments, an engine may include electric motors, sonic wave generators, etc.

In some embodiments, mobilizing secretions may include generating increased airflow velocities and/or percussive or oscillation forces resulting in cough-like shear forces. In some embodiments, mobilizing secretions may include decreasing a viscosity of at least some secretions in an airway within the subject substantially adjacent the first and/or second zone. Mobilizing secretions may assist subjects to move retained secretions from smaller airways to larger airways where they may move more easily via coughing. In some embodiments, secretions may include what is generally referred to as mucus. Mucus may include water, ions, soluble mediators, inflammatory cells, and/or secreted mucins. In some embodiments, secretions may include any fluids (e.g., excessive fluids) potentially blocking subject airways.

In some embodiments, adjusting the wearable system may include adjusting fastening systems which couple the wearable system to the subject. In some embodiments, the wearable system may be adjustable at least across a chest and/or portion of a torso of a subject (e.g., as depicted in FIG. 1 using friction fittings and straps 120). In some embodiments, the wearable system may be adjustable at least across one or more shoulders of a subject (e.g., as depicted in FIG. 1). In some embodiments, the wearable system may be adjustable using one or more fasteners 130 using at least one type of fastener. In some embodiments, adjusting the wearable system may include positioning the first engine or the second engine (e.g., and possibly additional engines) relative to the first zone or the second zone (e.g., and possibly additional zones) respectively. In some embodiments, a fastener may include a plurality of snaps 130 coupling the wearable system across the shoulder of a subject (e.g., as depicted in FIG. 1) such that the engines may positioned appropriately relative to the airways of the subject. By attaching the fasteners in different combinations with one another the engines may be adjusted relative to the subject.

Figure 6:
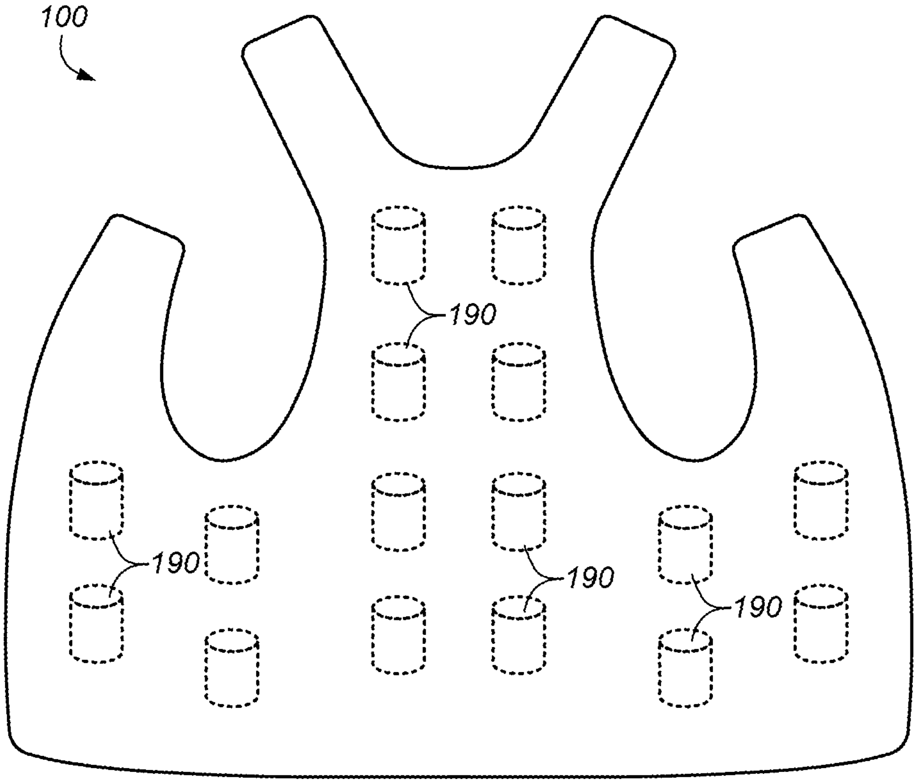
FIG. 6 depicts a front perspective view of a representation of an embodiment of a portable high frequency chest wall oscillator harness using sealable containers coupling system positioned on a subject.

In some embodiments, engines may be repositioned or adjusted relative to a subject using a system (e.g., by a doctor) which inhibits a subject from repositioning the engines once positioned. For example, a wearable garment may include a plurality of pockets or containers which engines may be positioned in and then sealed in. FIG. 6 depicts a front perspective view of a representation of an embodiment of a wearable system 100 using a plurality of sealable containers 190 coupling system used to couple the engines to the wearable system.

Figure 3:
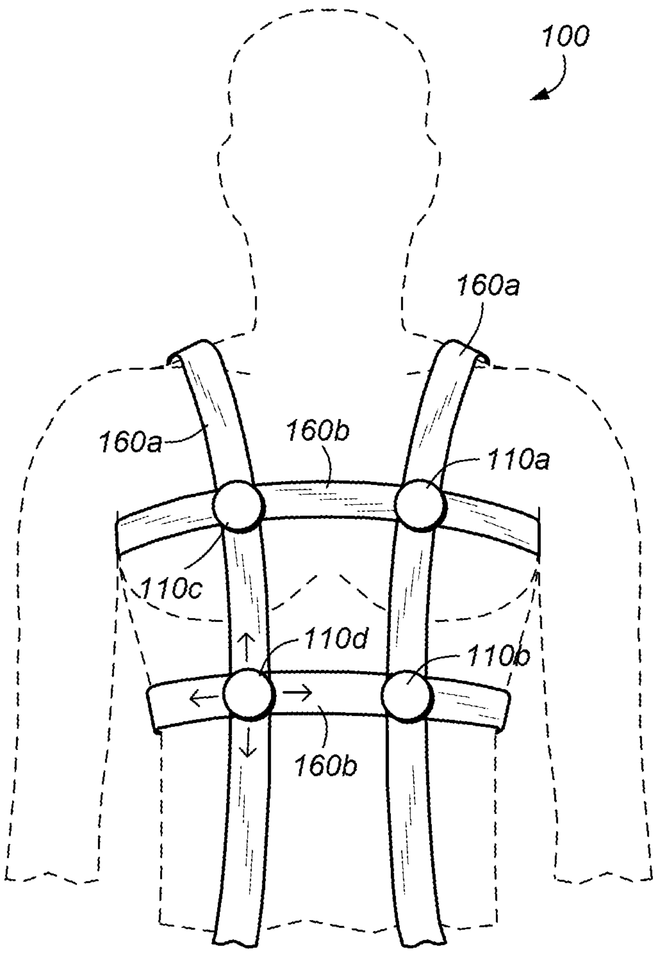
FIG. 3 depicts a front perspective view of a representation of an embodiment of a portable high frequency chest wall oscillator harness.

In some embodiments, the system may include a wearable system (e.g., as depicted in FIG. 1) which resembles a vest (e.g., coupled or directly attached at least across a front, side, and/or back). In some embodiments, the system may include a wearable system which includes a plurality of bands and/or straps 160 (e.g., as depicted in FIG. 3). FIG. 3 depicts a front perspective view of a representation of an embodiment of a portable high frequency chest wall oscillator harness 100. In some embodiments, the bands 160 (e.g., as depicted in FIG. 3) may be incorporated into a vest (e.g., as depicted in FIG. 1). The engines 110*a-d* may be coupled or directly attached to the bands. The engines may be coupled or directly attached to the bands such that the engines are positionable along the bands. The bands may include vertical bands 160*a* and horizontal bands 160*b*. Positionable engines may allow the engines to be positioned appropriately to provide the greatest benefit to the subject.

Figure 4A:
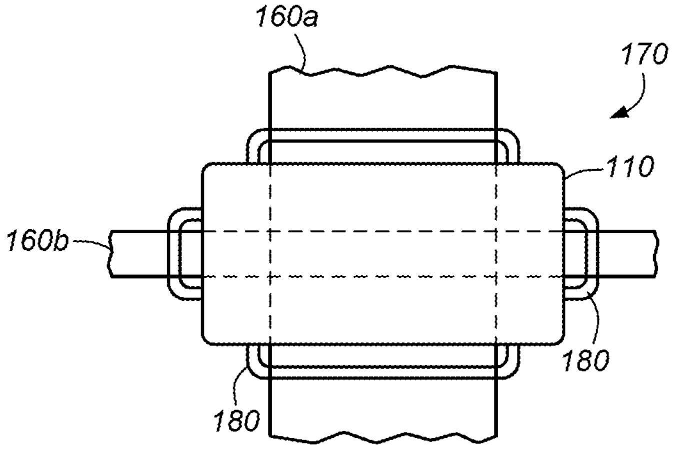
FIG. 4A depicts a front view of a representation of an embodiment of an engine coupling system.
Figure 4B:
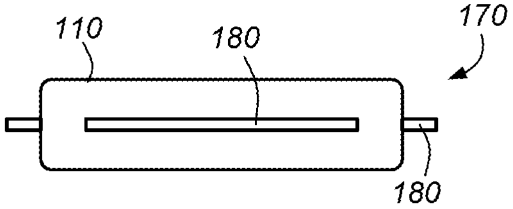
FIG. 4B depicts a side view of a representation of an embodiment of an engine coupling system.
Figure 5:
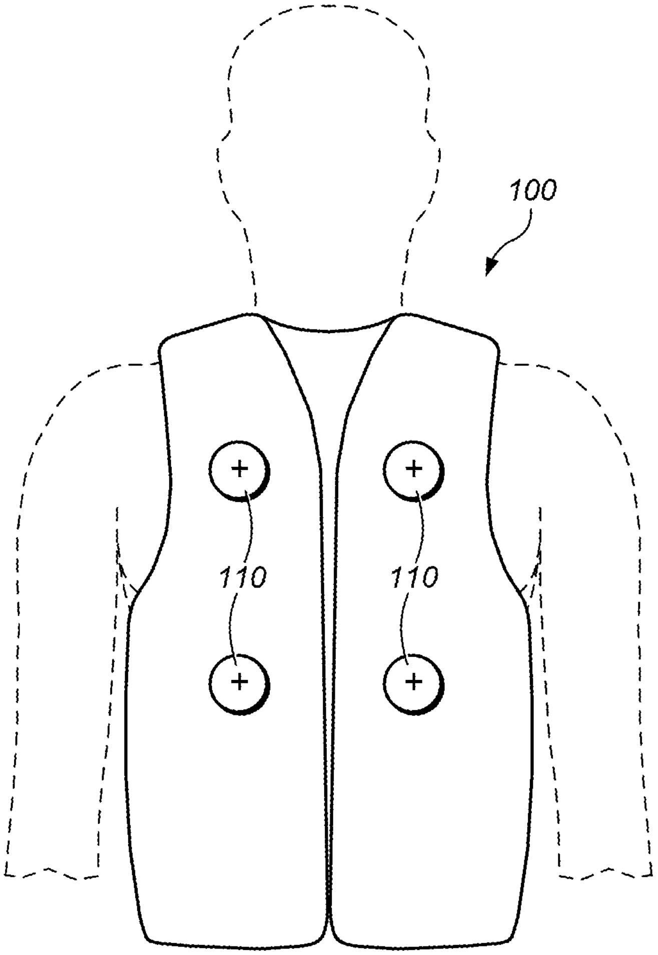
FIG. 5 depicts a front perspective view of a representation of an embodiment of a portable high frequency chest wall oscillator harness using a hook and loop coupling system positioned on a subject.

The engines may be positionally coupled or directly attached to the bands and/or system using a number of means known such that the engines may be repositioned during use as appropriate for individual subjects. In some embodiments, a hook and loop system may be used to couple the engines to a wearable system such that the engines are repositionable. FIG. 5 depicts a front perspective view of a representation of an embodiment of a wearable system 100 using a hook and loop system to couple engines 100 to the system. In some embodiments, a cleat 170 may be used to couple the engine to one or more of the bands. FIG. 4A depicts a front view of a representation of an embodiment of an engine coupling system 170. FIG. 4B depicts a side view of a representation of an embodiment of an engine coupling system 170. The cleat may include a locking mechanism 180 which once locked may inhibit movement of the cleat along the band(s). In some embodiments, a coupling mechanism may couple a horizontal band 160*b* to a vertical band 160*a* such that engines are repositioned relative to the subject by repositioning the bands relative to one another. The bands may include coupling mechanisms as depicted in FIG. 1 in order to couple the bands to a subject. The lengths of the bands may be adjustable as well in order to fit the bands to the subject.

In some embodiments, the wearable system 100 may include multiple engines 110 (e.g., eight or more engines). The system may include at least four engines 110, at least six engines 110, or at least eight engines 110 (e.g., as depicted in FIG. 1, although only the front four are depicted, the remaining four are on the back of the system 100). In some embodiments, the system may include eight engines. In some embodiments, the method may include adjusting the wearable system comprises positioning a third engine or a fourth engine relative to the first zone or the second zone respectively on an opposing side of the subject opposite of the side of the first and the second engine.

In some embodiments, the system 100 may include a control unit 140. The method may include activating at least the first engine using the control unit 140. The control unit may control activation/deactivation/adjustment of all of the engines of the system 100. In some embodiments, the control unit 140 may be couplable to the system 100 (e.g., using a flap of material which may be used to cover and protect the control unit as depicted in FIG. 1). The control unit 140 may be directly wired to the engines 110 and/or may be wirelessly coupled or directly attached to the engines. The control unit may use any number of known input methods (e.g., including touchpad). The control unit may be digital or analog. In some embodiments, the control unit may adjust one or more settings of the engines. The control unit may adjust the oscillation force output by the engine. The control unit may adjust an amplitude of the oscillation force output by the engine. The control unit may adjust a frequency of the oscillation force output by the engine. In some embodiments, engine parameters may be adjusted via software (e.g., a phone app) remotely (e.g., Wi-Fi, Bluetooth, etc.). In some embodiments, the engines 110 may include a frequency range from 5 Hz to 20 Hz. In some embodiments, the intensity levels dictate the frequency which generally runs at 5 Hz for the lowest setting, 13 Hz for the medium setting and 20 Hz for the highest setting.

In some embodiments, a method may include modifying the treatment parameters (e.g. amplitude, frequency, and time for each engine). Each engine may be programmed, using physical hardware control unit or software to run a custom cycle. This programming may be performed by the subject. In addition, the system may provide a physician or caregiver with the ability to prescribe a defined treatment and to inhibit the user from modifying the treatment settings (e.g. lock-out feature w/password, pin code, etc.).

In some embodiments, the method and/or system may adaptively modify the treatment protocol based on subject and/or physician feedback. For example, a subject enters mucus secretion levels after each treatment and the system adaptively optimizes the treatment settings over time.

In some embodiments, the method and/or system may monitor compliance for each subject, including parameters run, time of treatment, information. For example, the system could monitor (in real-time) the treatment time of day and any subject feedback. This could be accomplished through hardware or software (e.g. a web-based subject/physician portal which links w/Bluetooth to each vest). The information may be provided to the subject, physician, insurance company or other third-party.

In some embodiments, the system 100 may include at least one battery 150. The method may include powering at least the first engine 110*a* using one or more batteries 150 coupled or directly attached to the wearable system. In some embodiments, a battery 150 may include a rechargeable battery and/or a disposable battery. The battery 150 may include two or more batteries. The batteries 150 may be easily swapped out whether rechargeable or disposable. The battery 150 may be coupled or directly attached to the system 100 (e.g., using a flap of material which may be used to cover and protect the battery as depicted in FIG. 1). The system may include an adapter such that when necessary the system may be coupled or directly attached to an electrical outlet (e.g., through an electrical adapter if necessary). The system 100 may be powered using AC or DC power sources such that the system may be powered using virtually any known power source currently available.

In some embodiments, the system may be self-contained. The system may be self-contained such that a subject may wear the system 100 and move freely and in a substantially unrestricted manner. The system may be self-contained such that a subject may wear the system 100 while functioning and not physically connected to any external devices (e.g., air pumps).

Upper Chest Portable High Frequency Physiological Oscillator

In some embodiments, a system and/or method may include clearing a biological airway(s). As discussed though even wearable systems as described herein may not be sufficient to assist a subject in fully clearing the subject's biological airway. In some instances secretions may be moved out of the lungs but not high enough into the major bronchial tubes and/or trachea such that a subject may evacuate the secretions from the subject (especially with the reduced air capacity of the subject who need to employ systems as described herein). It would be beneficial to have a system which works alone or in combination with the vest/harnesses described herein to further move a subject's secretions out of the subject's airways.

In some embodiments, the method may include positioning a wearable system around a subject's neck. The wearable system may be coupled or directly attached to another wearable garment such that the wearable system is positioned substantially around at least a portion of the subject's neck. The method may include adjusting the wearable system such that an oscillation force is applied to at least an upper first zone of the subject. The upper first zone may be proximate to a collarbone of the subject and proximate to a juxtaposition of the subject's bronchial tubes and trachea on a first side of the subject. The method may include applying the oscillation force to at least upper first zone using an upper first engine. The method may include mobilizing at least some secretions in an airway within the subject substantially adjacent the first zone so that it may be expelled by the subject.

Figure 7:
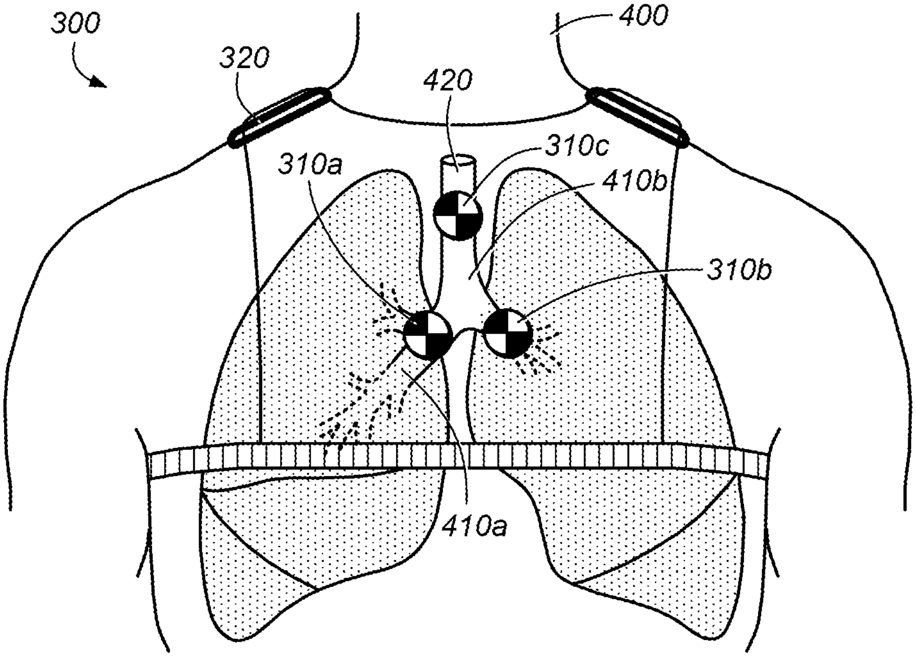
FIG. 7 depicts a representation of an embodiment of a portable high frequency physiological oscillator harness positioned around a subject's neck.

FIG. 7 depicts a representation of an embodiment of a portable high frequency physiological oscillator harness 300 positioned around a subject's neck 400. In some embodiments, the upper first engine 310 may include one or more engines. The engines may be separately powered and/or controlled. The upper first engine may include at least three engines 310*a-c*. In some embodiments, a first 310*a* of the three engines may be positioned proximate a first bronchial tube 410*a* extending from the juxtaposition. A second 310*b* of the three engines may be positioned proximate a second bronchial tube 410*b* extending from the juxtaposition. A third 310*c* of the three engines may be positioned proximate the trachea 420. Positioning at least one (e.g., three) engine in such a fashion may assist a subject in clearing secretions out of the subject's airways, especially when used in combination with the vest/harness described herein. The vest/harness described herein may assist in moving secretions from a subject's airways in the lungs up into the at least major bronchial passages adjacent/in the upper first zone wherein the wearable system may further move the subject's secretions out of the subject.

In some embodiments, the method may include adjusting the wearable system such that the oscillation force is applied to at least an upper second zone of the subject. The upper second zone may be proximate to the collarbone of the subject and proximate to the juxtaposition of the subject's bronchial tubes and trachea. The upper second zone may be positioned on a second side of the subject, wherein the second side is on an opposing side of the subject from the first side. The method may include applying the oscillation force to the at least upper second zone using an upper second engine. The upper second engine may include at least one (e.g., three) engines.

Figure 8:
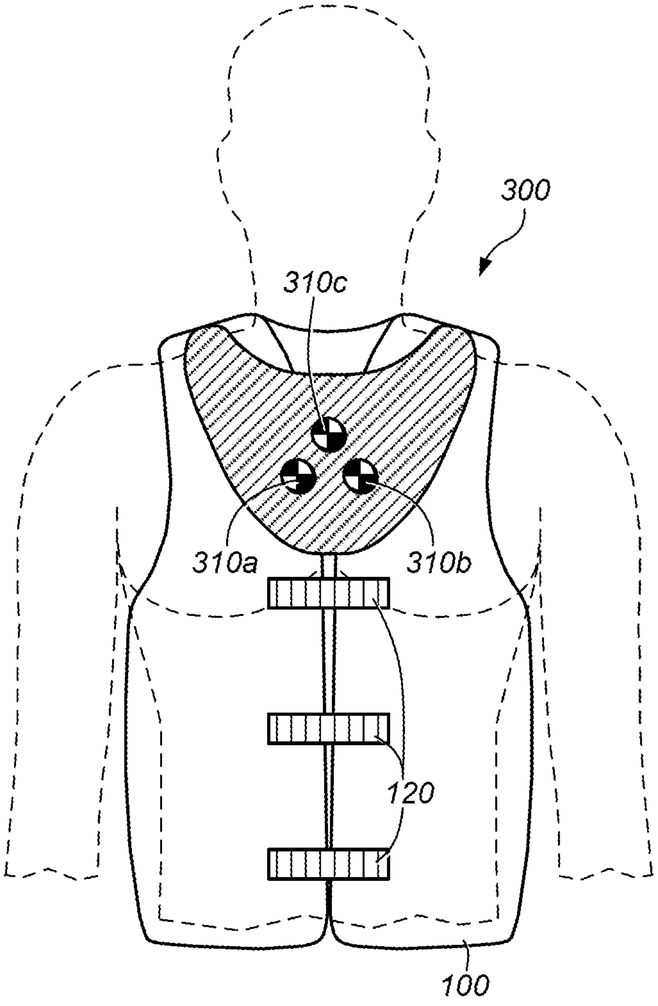
FIG. 8 depicts a representation of an embodiment of a portable high frequency physiological oscillator harness positioned around a subject's neck in combination with portable high frequency chest wall oscillator vest.

In some embodiments, the wearable system 300 may include adjustable fastening systems 320 which couple the wearable system to the subject. Adjustable fastening systems may include snaps buckles, Velcro, etc. FIG. 8 depicts a representation of an embodiment of a portable high frequency physiological oscillator harness positioned around a subject's neck in combination with portable high frequency chest wall oscillator vest. The wearable system 300 may be used in combination with other systems which function to mobilize internal lung secretions. The wearable system 300 may be used without any other systems in order to mobilize internal lung secretions such that the secretions are expelled out of the subject.

In some embodiments, the system 300 may include a control unit 140 (e.g., a control unit of the system 300 may function independently of other possible control units, a control unit of the system 300 may be electrically coupled or directly attached to the control unit of the vest when used in combination with the vest, or the system 300 may not include an independent control unit and the system 300 may be coupled or directly attached into a control unit of a wearable system 100). The method may include activating at least the upper first engine using the control unit 140. The control unit may control activation/deactivation/adjustment of all of the engines of the system 300. In some embodiments, the control unit 140 may be couplable to the system 300 (e.g., using a flap of material which may be used to cover and protect the control unit). The control unit 140 may be directly wired to the engines 310 and/or may be wirelessly coupled or directly attached to the engines. The control unit may use any number of known input methods (e.g., including touchpad). The control unit may be digital or analog. In some embodiments, the control unit may adjust one or more settings of the engines. The control unit may adjust the oscillation force output by the engine. The control unit may adjust an amplitude of the oscillation force output by the engine. The control unit may adjust a frequency of the oscillation force output by the engine. In some embodiments, engine parameters may be adjusted via software (e.g., a phone app) remotely (e.g., Wi-Fi, Bluetooth, etc.). In some embodiments, the engines 310 may include a frequency range from 5 Hz to 20 Hz. In some embodiments, the intensity levels dictate the frequency which generally runs at 5 Hz for the lowest setting, 13 Hz for the medium setting and 20 Hz for the highest setting.

In some embodiments, a method may include modifying the treatment parameters (e.g. amplitude, frequency, and time for each engine). Each engine may be programmed, using physical hardware control unit or software to run a custom cycle. This programming may be performed by the subject. In addition, the system may provide a physician or caregiver with the ability to prescribe a defined treatment and to inhibit the user from modifying the treatment settings (e.g. lock-out feature w/password, pin code, etc.).

In some embodiments, the method and/or system may adaptively modify the treatment protocol based on subject and/or physician feedback. For example, a subject enters mucus secretion levels after each treatment and the system adaptively optimizes the treatment settings over time.

In some embodiments, the method and/or system may monitor compliance information. For example, the system could monitor (in real-time) the treatment for each subject, including parameters run, time of treatment, time of day and any subject feedback. This could be accomplished through hardware or software (e.g. a web-based subject/physician portal which links w/Bluetooth to each vest). The information may be provided to the subject, physician, insurance company or other third-party.

In some embodiments, the system 300 may include at least one battery 150 (e.g., a battery of the system 300 may function independently of other possible batteries, a battery of the system 300 may be electrically coupled or directly attached to the battery of the vest when used in combination with the vest, or the system 300 may not include an independent battery and the system 300 may be coupled or directly attached into a battery of a wearable system 100). The method may include powering at least the upper first engines 310 using one or more batteries 150 coupled or directly attached to the wearable system. In some embodiments, a battery 150 may include a rechargeable battery and/or a disposable battery. The battery 150 may include two or more batteries. The batteries 150 may be easily swapped out whether rechargeable or disposable. The battery 150 may be coupled or directly attached to the system 300 (e.g., using a flap of material which may be used to cover and protect the battery). The system may include an adapter such that when necessary the system may be coupled or directly attached to an electrical outlet (e.g., through an electrical adapter if necessary). The system 300 may be powered using AC or DC power sources such that the system may be powered using virtually any known power source currently available.

In some embodiments, the system may be self-contained. The system may be self-contained such that a subject may wear the system 300 and move freely and in a substantially unrestricted manner. The system may be self-contained such that a subject may wear the system 300 while functioning and not physically connected to any external devices (e.g., air pumps).

Positionable Oscillating Motor Array with Potentially Disposable and/or Recyclable Portions In some embodiments, it is advantageous to form a wearable system with one or more disposable portions. There are many advantages to having a wearable system formed from at least in part disposable portions including facilitating use of the wearable system in different environments (e.g., hospitals, clinics, etc.). Professional healthcare environments are required to constantly be vigilant regarding sanitation and cross contamination between patients. To this end medical equipment must be sanitized before being used again. However, sanitizing equipment is typically time consuming and/or expensive. As such much of the equipment used in healthcare environments which comes into direct contact with subjects is disposable (or covered by disposable sheaths). It is typically much easier and/or less expensive to throw away equipment which comes into contact with subjects as opposed to cleaning the equipment.

The method may include positioning a wearable system on a subject. The method may include adjusting the wearable system such that an oscillation force is applied to at least a first zone and to at least a second zone of the subject (e.g., and possibly more zones). In some embodiments, the oscillation force may be infinitely adjustable relative to the subject. Having an infinitely adjustable oscillation force (e g, infinitely positionable engines) may allow customizable positioning of the oscillation force as required by the subject (e.g., as prescribed by a care giver (e.g., doctor, nurse, etc.).

In some embodiments, mobilizing secretions may include generating increased airflow velocities and/or percussive or oscillation forces resulting in cough-like shear forces. In some embodiments, mobilizing secretions may include decreasing a viscosity of at least some secretions in an airway within the subject substantially adjacent the first and/or second zone. Mobilizing secretions may assist subjects to move retained secretions from smaller airways to larger airways where they may move more easily via coughing. In some embodiments, secretions may include what is generally referred to as mucus. Mucus may include water, ions, soluble mediators, inflammatory cells, and/or secreted mucins. In some embodiments, secretions may include any fluids (e.g., excessive fluids) potentially blocking subject airways.

Figure 9A:
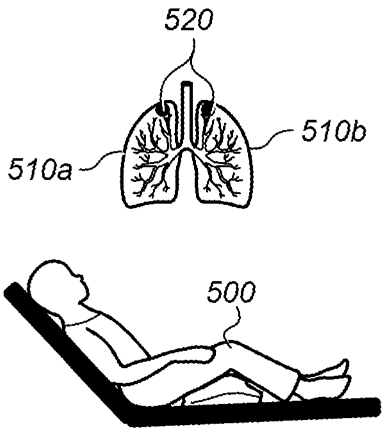
FIGS. 9A-J depict representations of different areas of a subject's lungs which may require treatment using herein described systems and methods.
Figure 9B:
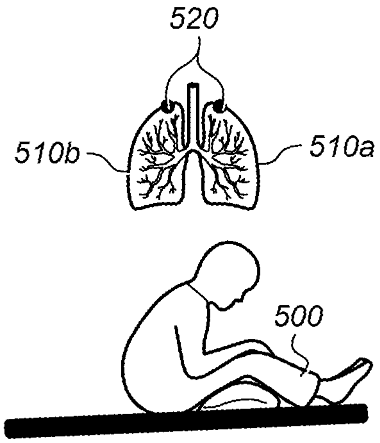
Figure 9C:
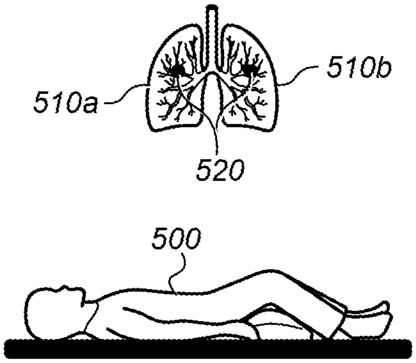
Figure 9D:
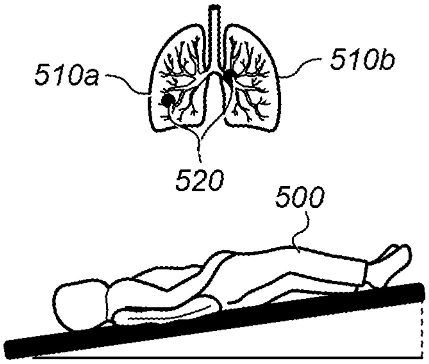
Figure 9E:
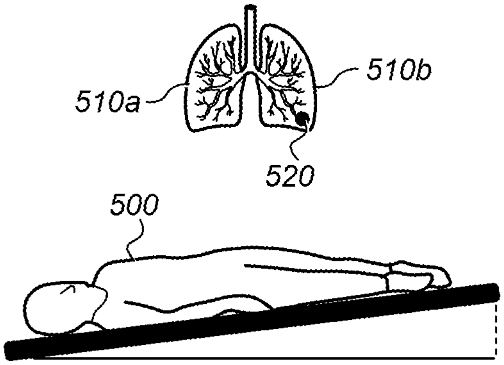
Figure 9F:
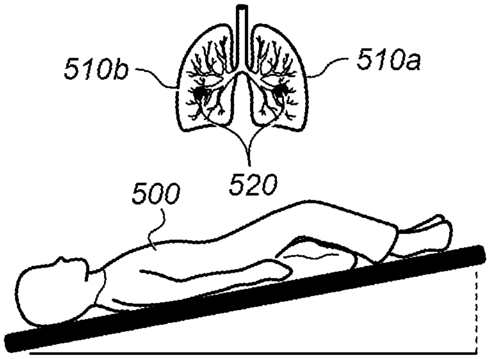
Figure 9G:
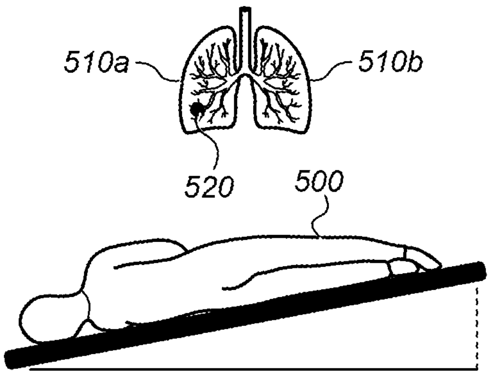
Figure 9H:
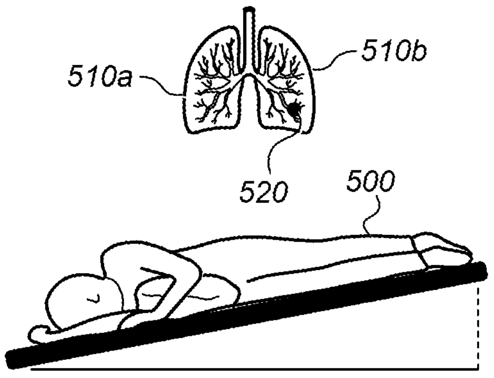
Figure 9I:
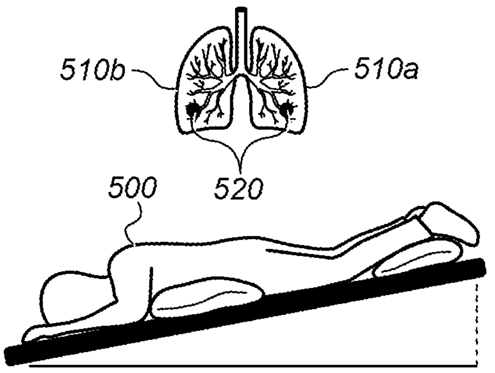
Figure 9J:
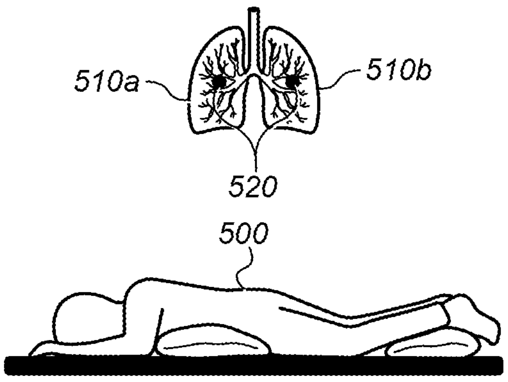

Depending upon the subject's specific condition one or more engines may be positioned accordingly (e.g., around the area of trouble for the subject which require treatment). FIGS. 9A-J depict representations of different areas of a subject's lungs 510*a-b* which may require treatment using herein described systems and methods. FIGS. 9A-J depict representations of right lung 510*a* and left lung 510*b* of subject 500. Zones 520 of lungs 510 are examples of areas in a subject which may need treatment and/or wherein treatment may be applied as prescribed by a physician for treatment. FIGS. 9A-J depict representations of subject 500 positioned for extracting fluids from lungs 510 using known percussion methods. In some embodiments, positioning the subject 500, as depicted in FIGS. 9A-J for example, may be used in combination with the systems and methods described herein. In some embodiments, any special positioning of the subject may not be necessary and/or used in combination with the systems and methods described herein. FIG. 9A depicts subject 500 positioning and/or zones 520 for treating (e.g., applying oscillation forces using systems and methods described herein) respiratory afflictions affecting the left and right anterior apical portions of lungs 510. FIG. 9B depicts subject 500 positioning and/or zones 520 for treating (e.g., applying oscillation forces using systems and methods described herein) respiratory afflictions affecting the left and right posterior apical portions of lungs 510. FIG. 9C depicts subject 500 positioning and/or zones 520 for treating (e.g., applying oscillation forces using systems and methods described herein) respiratory afflictions affecting the left and right anterior segments of lungs 510. FIG. 9D depicts subject 500 positioning and/or zones 520 for treating (e.g., applying oscillation forces using systems and methods described herein) respiratory afflictions affecting the right middle lobe portion of lung 510. FIG. 9E depicts subject 500 positioning and/or zones 520 for treating (e.g., applying oscillation forces using systems and methods described herein) respiratory afflictions affecting the left singular portion of lung 510. FIG. 9F depicts subject 500 positioning and/or zones 520 for treating (e.g., applying oscillation forces using systems and methods described herein) respiratory afflictions affecting the left and right anterior basil portions of lungs 510. FIG. 9G depicts subject 500 positioning and/or zones 520 for treating (e.g., applying oscillation forces using systems and methods described herein) respiratory afflictions affecting the right lateral basal portion of lung 510. FIG. 9H depicts subject 500 positioning and/or zones 520 for treating (e.g., applying oscillation forces using systems and methods described herein) respiratory afflictions affecting the left lateral basal portion of lung 510. FIG. 9I depicts subject 500 positioning and/or zones 520 for treating (e.g., applying oscillation forces using systems and methods described herein) respiratory afflictions affecting the left and right posterior basal portions of lungs 510. FIG. 9J depicts subject 500 positioning and/or zones 520 for treating (e.g., applying oscillation forces using systems and methods described herein) respiratory afflictions affecting the left and right superior basal portions of lungs 510. FIGS. 9A-J depict representations of how systems described herein may be used as examples of prescriptive positioning of engines by a caregiver.

Figure 10:
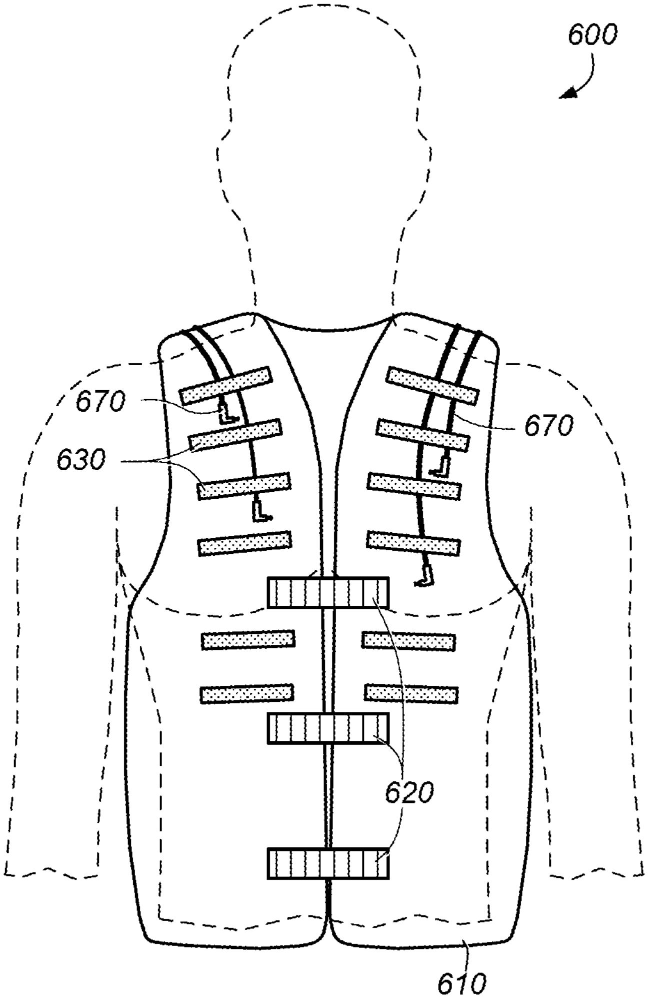
FIG. 10 depicts a front view of a representation of an embodiment of a portable high frequency chest wall oscillator inner harness positioned on a subject.

FIG. 10 depicts a front perspective view of a representation of an embodiment of a portable high frequency chest wall inner harness 610 of an oscillator system 600. Known HFCWO systems do not allow for a user adjusting where forces are applied to on the subject. This is problematic because although some known HFCWO systems may come in different sizes to accommodate differently sized subjects, there are far too many people of different sizes and so it is impractical to produce enough differently sized systems for all of the differently sized subjects. A system 600 which allows for adjustment and/or positioning of one or more engines and/or one or more groups of engines may allow for prescriptive oscillation or prescriptive positioning of engines by a caregiver. For example, a caregiver may employ means to visualize (e.g., x-rays) secretions accumulating in the lungs of a subject and then position engines appropriately around any areas where secretions are accumulating. In some embodiments, engines may not only be simply placed adjacent treatment areas but also may be positioned adjacent to areas adjacent to the treatment area to assist in flushing out secretions from the subject (e.g., pushing the secretions outside of the subject). In some embodiments, engines may be positioned in a serpentine pattern on a subject using systems described herein to create what may be described as a wave effect of oscillation forces.

In some embodiments, a caregiver may prescribe not only the position of the engines but also the frequency of one or more of the engines. The pulse or the beat frequency of one or more of the engines may be adjusted based upon a prescribed frequency. In some embodiments, a caregiver may prescribe or program one or more or all of the engines to turn on or off.

FIG. 10 depicts a front perspective view of a representation of an embodiment of a portable high frequency chest wall inner (or first) harness 610 of an oscillator system 600. In some embodiments, inner harness 610 may be sold in multiple sizes (e.g., 3 or more sizes). The inner harness may be sold in 3 sizes (e.g., child size, small adult size, large adult size). In some embodiments, an inner harness may be custom made or sized for a subject. In some embodiments, the inner harness may be formed from a flexible, a pliable or non-rigid material (e.g., as depicted in FIGS. 10-17 and 18-25). A pliable material may allow the inner harness to fit a wider range of differently physically sized subjects. The flexible material may allow the inner harness to bunch up around a slighter framed subject once cinched up. As such an inner wearable system may initially hang loosely in some embodiments.

Figure 24:
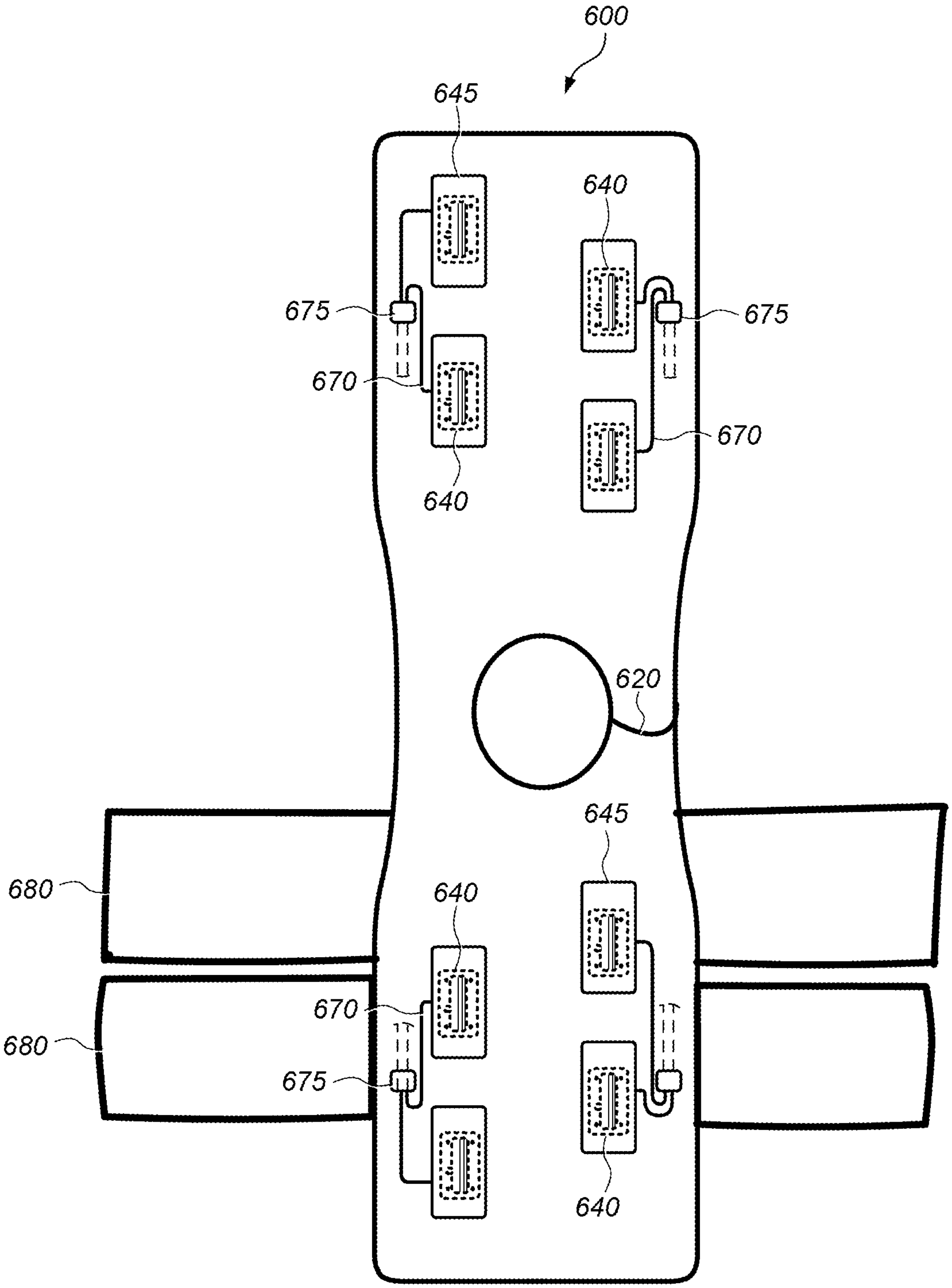
FIG. 24 depicts a front view of a representation of an embodiment of a portable high frequency chest wall oscillator inner harness including secured fasteners as well as two inactivated outer harnesses positioned on a subject.
Figure 25:
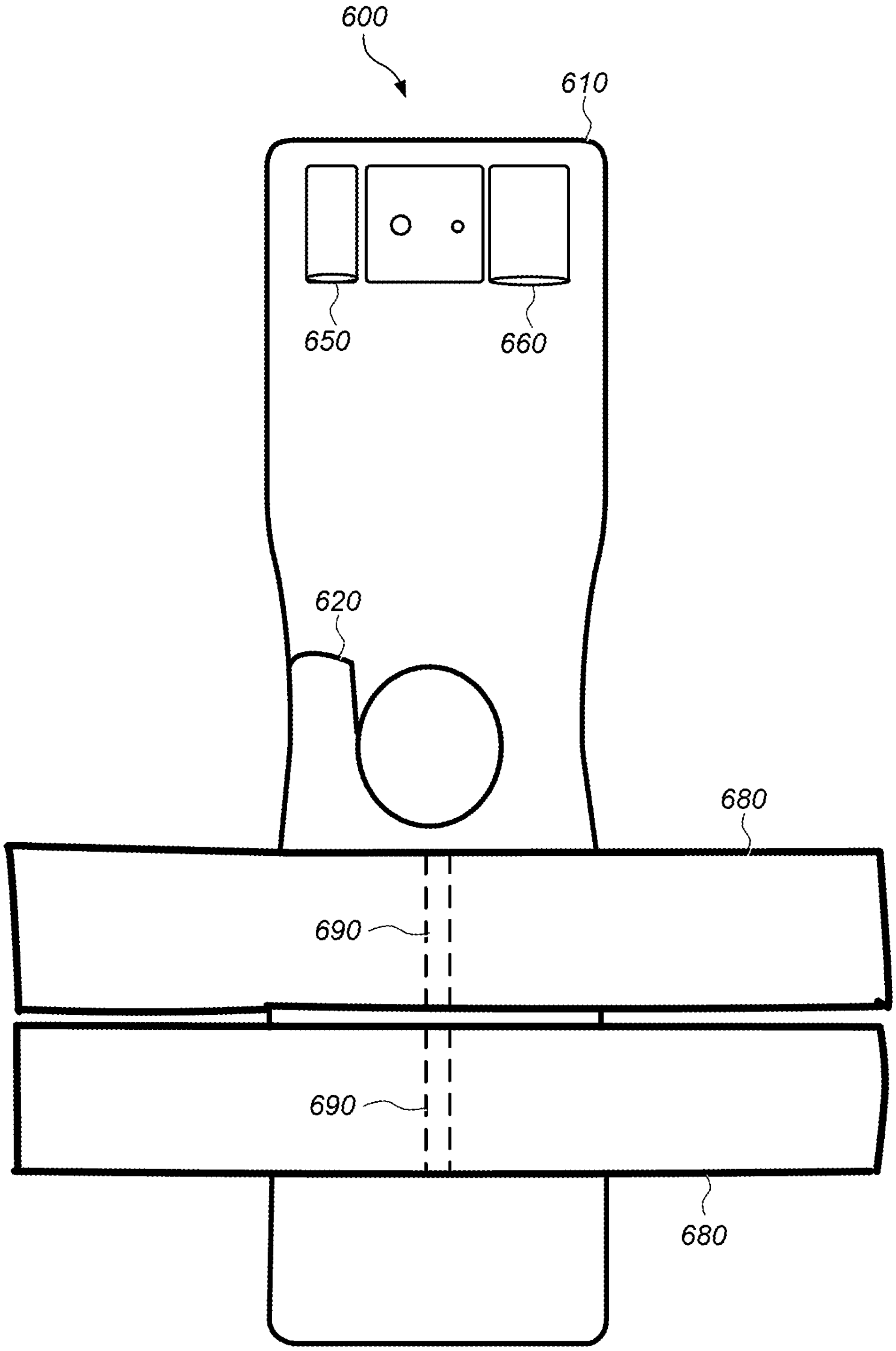
FIG. 25 depicts a front view of a representation of an embodiment of a portable high frequency chest wall oscillator inner harness including secured fasteners as well as two activated outer harnesses positioned on a subject.

In some embodiments, adjusting the wearable system inner harness may include adjusting fastening systems which couple the wearable system to the subject. In some embodiments, the wearable system may be adjustable at least across a chest and/or portion of a torso of a subject (e.g., as depicted in FIGS. 10, 10-17 and 18-23 using friction fittings and straps 620). In some embodiments, the wearable system may be adjustable at least across one or more shoulders of a subject (e.g., as depicted in FIGS. 1, 10-17 and 18-23) or one or more sides of a chest of a subject or a coupling system in a front of a subject (e.g., using zippers or lacing). In some embodiments, the wearable system may be adjustable using one or more fasteners. In some embodiments, the inner harness may include few or no size adjusting fasteners (e.g., as depicted in FIGS. 24-25).

In some embodiments, the inner harness may include a positioning system 630. The positioning system 630 may include a coupling method including, for example, a hook and loop coupling system which allows for positioning and coupling one or more portions of the oscillator system 600 to the inner harness. In some embodiments, a coupling method may include straps or pockets (e.g., as depicted in FIG. 6) used to position engines or other portions of the oscillator system 600.

In some embodiments, engines may be repositioned or adjusted relative to a subject using a system (e.g., by a doctor) which inhibits a subject from repositioning the engines once positioned.

Figure 11:
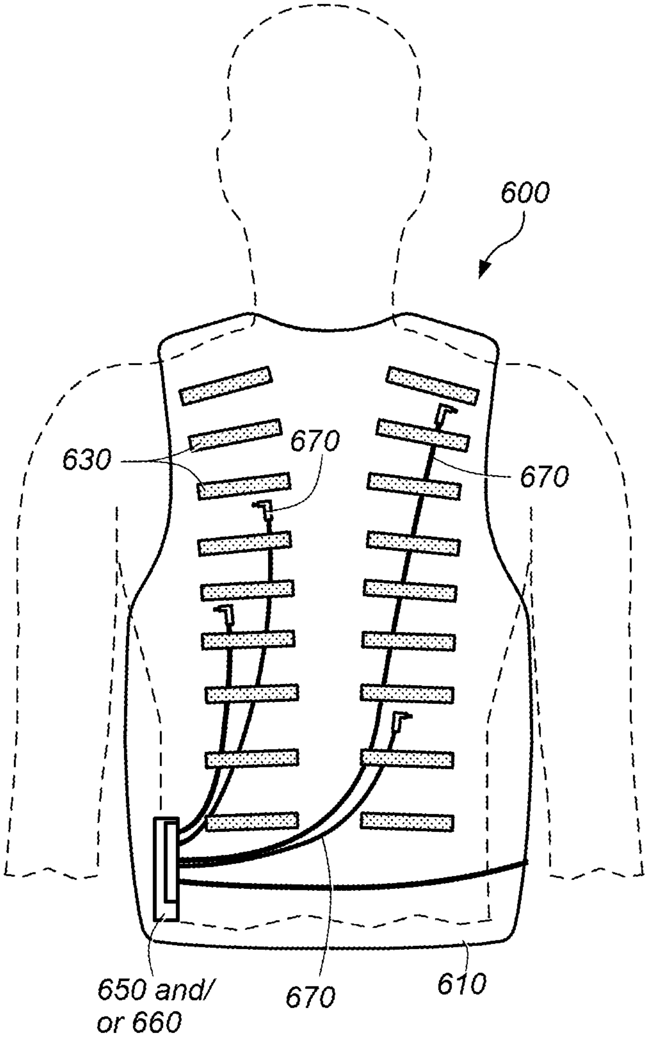
FIG. 11 depicts a rear view of a representation of an embodiment of a portable high frequency chest wall oscillator inner harness positioned on a subject.

The engines may be positionally coupled or directly attached to the bands and/or system using a number of means known such that the engines may be repositioned during use as appropriate for individual subjects. In some embodiments, a hook and loop system may be used to couple the engines to a wearable system such that the engines are repositionable. FIGS. 10-11 depict a front view and a rear view respectively of a representation of an embodiment of a portable high frequency chest wall oscillator inner harness 610 positioned on a subject. The embodiment depicted in FIGS. 10-11 includes positioning system 630 wherein the positioning system includes a plurality of hook and loop strips 630 for coupling portions of the oscillating system (e.g., engines 640, controller 650, battery 660, etc.) to the inner harness. The strips 630 depicted are just an example of a pattern of how the strips may be distributed on the harness. Specifically the strips may be positioned on the inner harness to allow positioning engines around the treatment areas as for example as depicted in FIGS. 9A-J.

Figure 12:
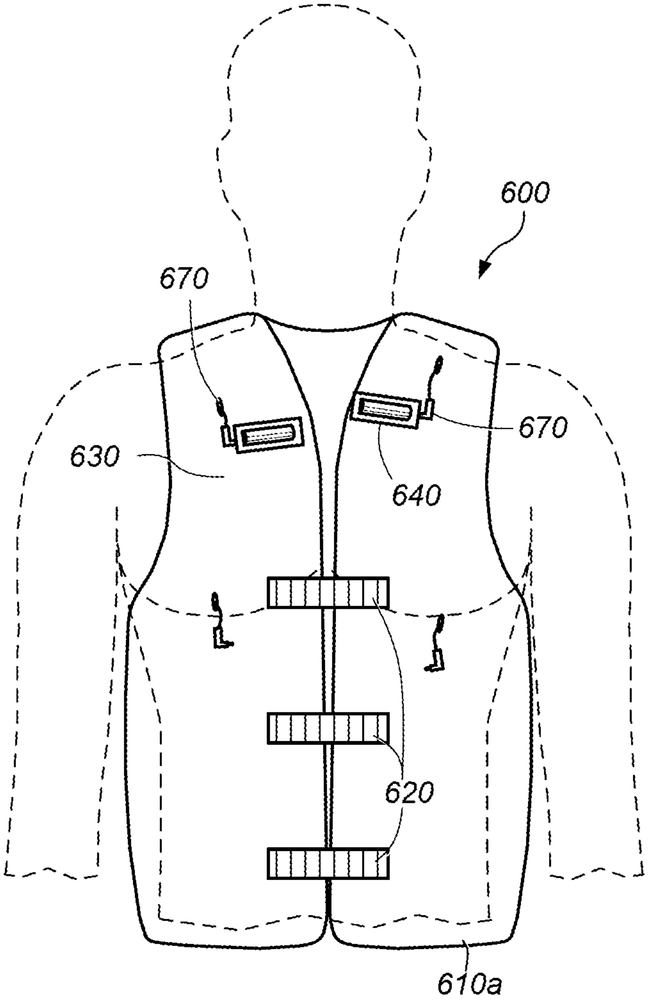
FIG. 12 depicts a front view of a representation of an embodiment of a portable high frequency chest wall oscillator inner harness positioned on a subject.
Figure 13:
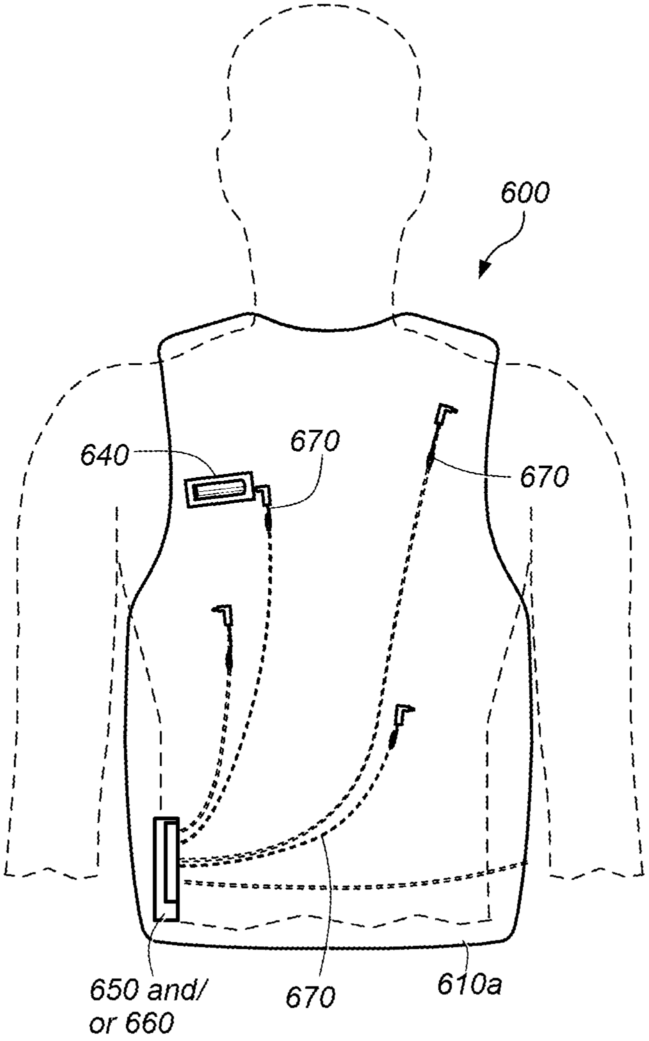
FIG. 13 depicts a rear view of a representation of an embodiment of a portable high frequency chest wall oscillator inner harness positioned on a subject.
Figure 14:
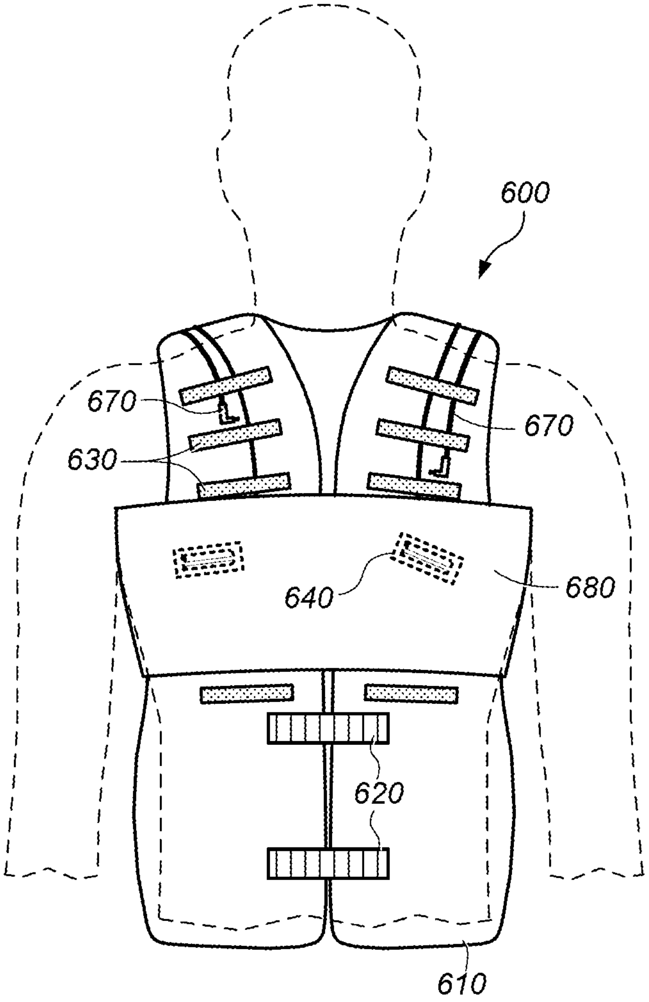
FIG. 14 depicts a front view of a representation of an embodiment of a portable high frequency chest wall oscillator inner harness and an outer harness positioned on a subject.
Figure 15:
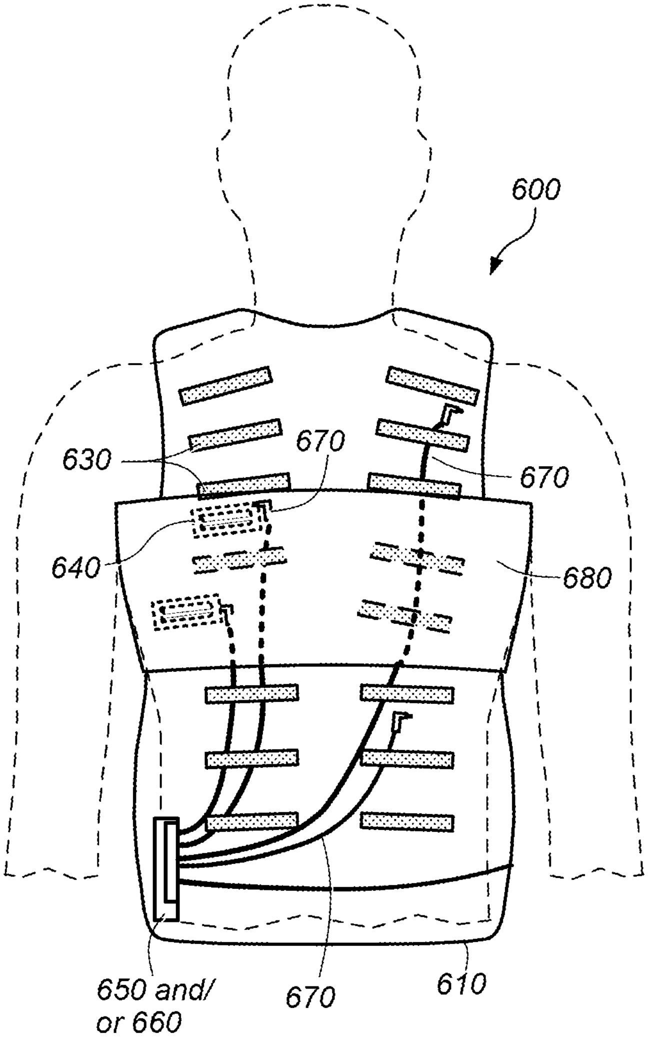
FIG. 15 depicts a rear view of a representation of an embodiment of a portable high frequency chest wall oscillator inner harness and an outer harness positioned on a subject.
Figure 16:
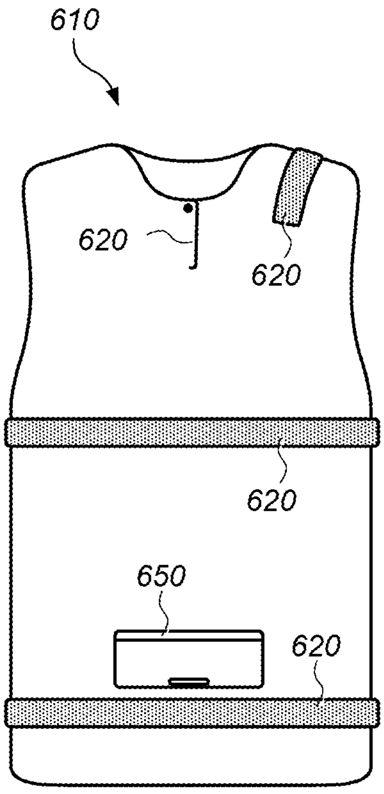
FIG. 16 depicts a front view of a representation of an embodiment of a portable high frequency chest wall oscillator inner harness.
Figure 17:
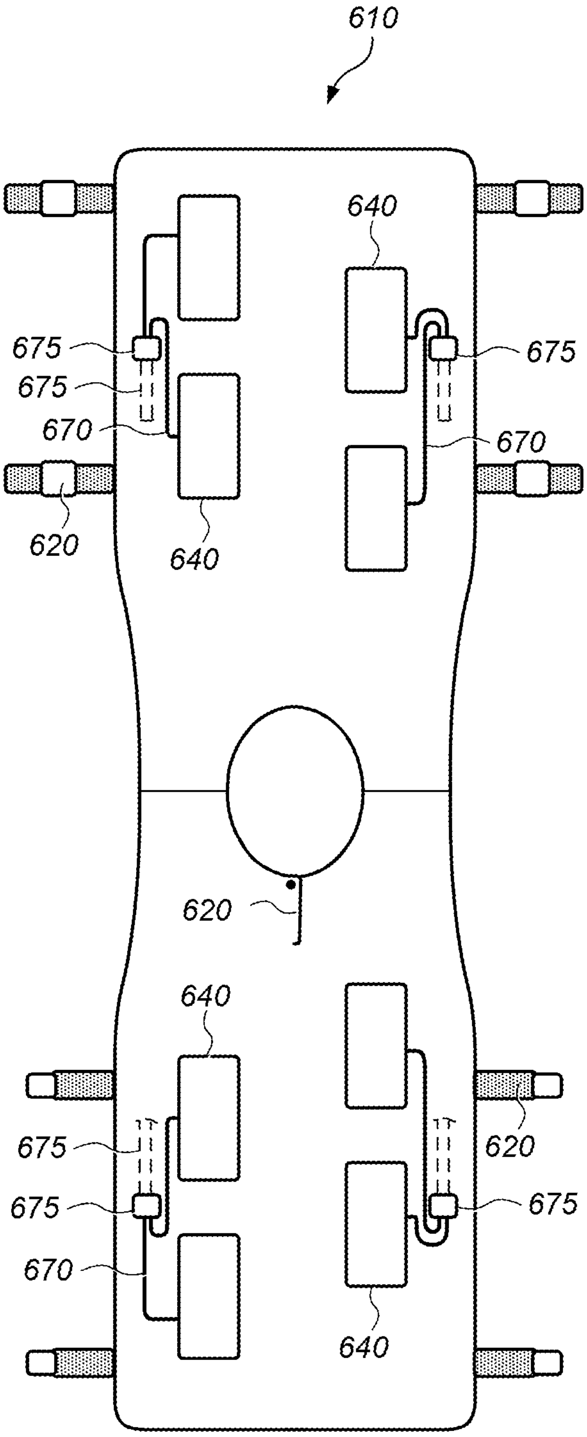
FIG. 17 depicts an interior view of a representation of an embodiment of a portable high frequency chest wall oscillator inner harness laid out in an open flat presentation.

In some embodiments, positioning system may include all (or substantially all) of the exterior surface of the inner harness (e.g., as depicted in FIGS. 10-15) being formed from half of a hook and loop system such that engines of the system 600 are virtually unlimited, in relation to the inner harness, as to where the portions may be positioned (the exterior surface may include a second layer formed from half of a hook and loop system). FIGS. 12-13 depict a front view and a rear view respectively of a representation of an embodiment of a portable high frequency chest wall oscillator inner harness positioned on a subject including a second layer 610*a* coupled or directly attached to the inner harness. In some embodiments, positioning system may include all (or substantially all) of the interior surface of the inner harness (e.g., as depicted in FIGS. 16-25) being formed from half of a hook and loop system such that engines of the system 600 are virtually unlimited, in relation to the inner harness, as to where the engines may be positioned (the interior surface may include a second layer formed from half of a hook and loop system). FIGS. 16-25 depict various views of a representation of an embodiment of a portable high frequency chest wall oscillator inner harness including a plurality of engines positioned on an interior surface of the inner wearable system.

Figure 20:
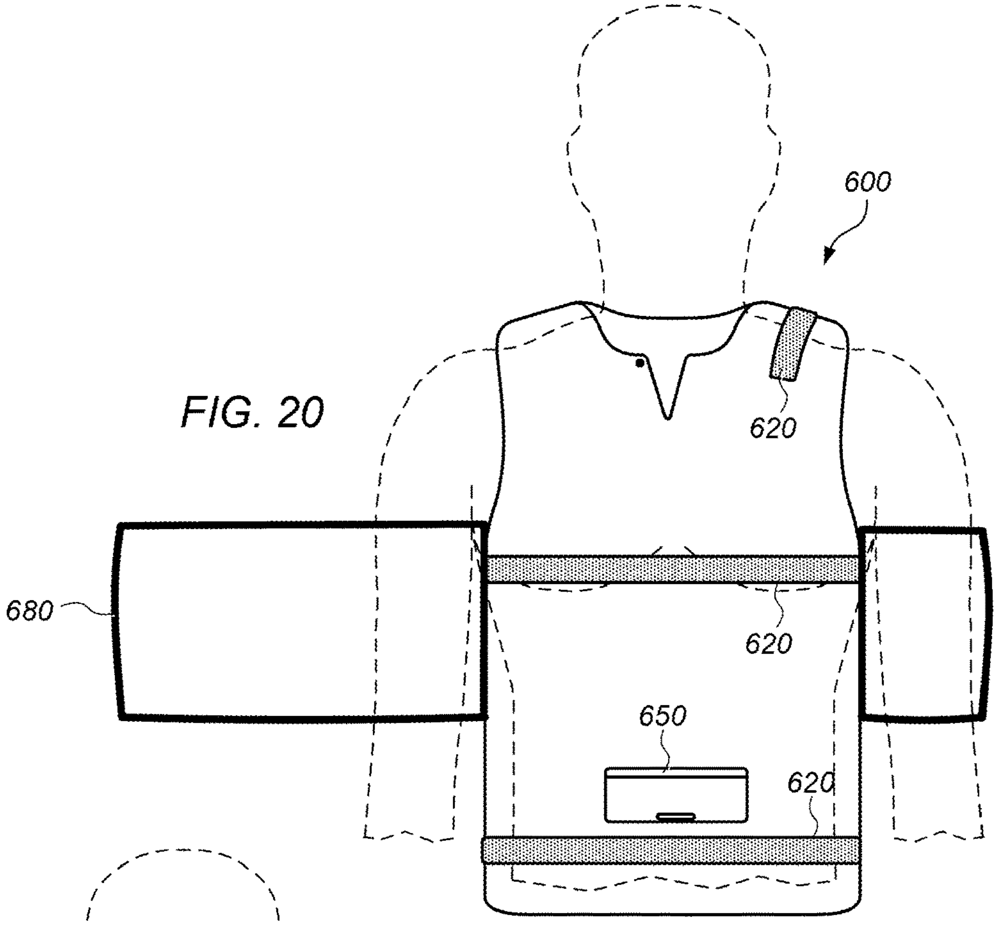
FIG. 20 depicts a front view of a representation of an embodiment of a portable high frequency chest wall oscillator inner harness including secured fasteners as well as an inactivated outer harness positioned on a subject.
Figure 21:
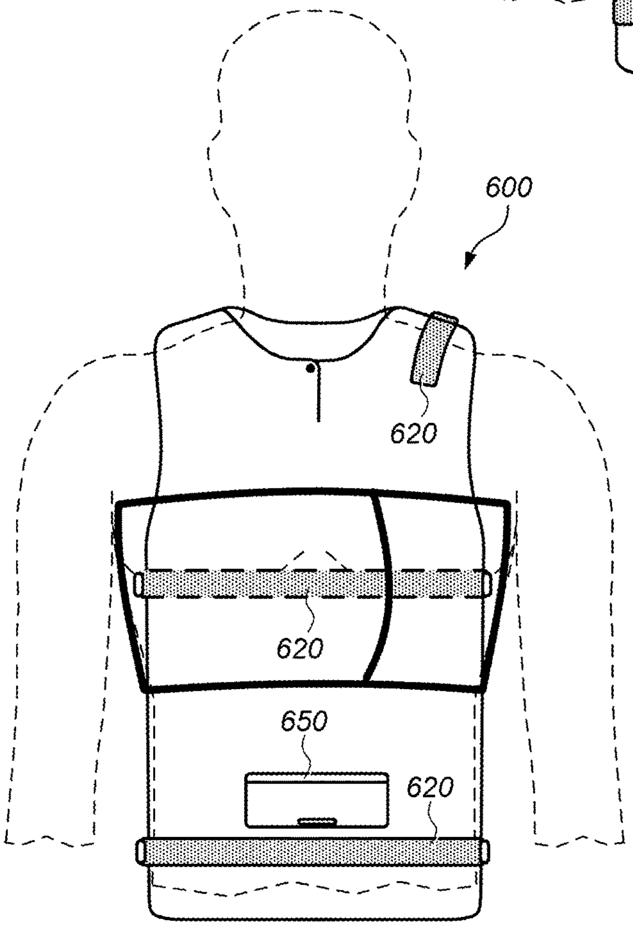
FIG. 21 depicts a front view of a representation of an embodiment of a portable high frequency chest wall oscillator inner harness including secured fasteners as well as a single activated outer harness positioned on a subject.
Figure 26:
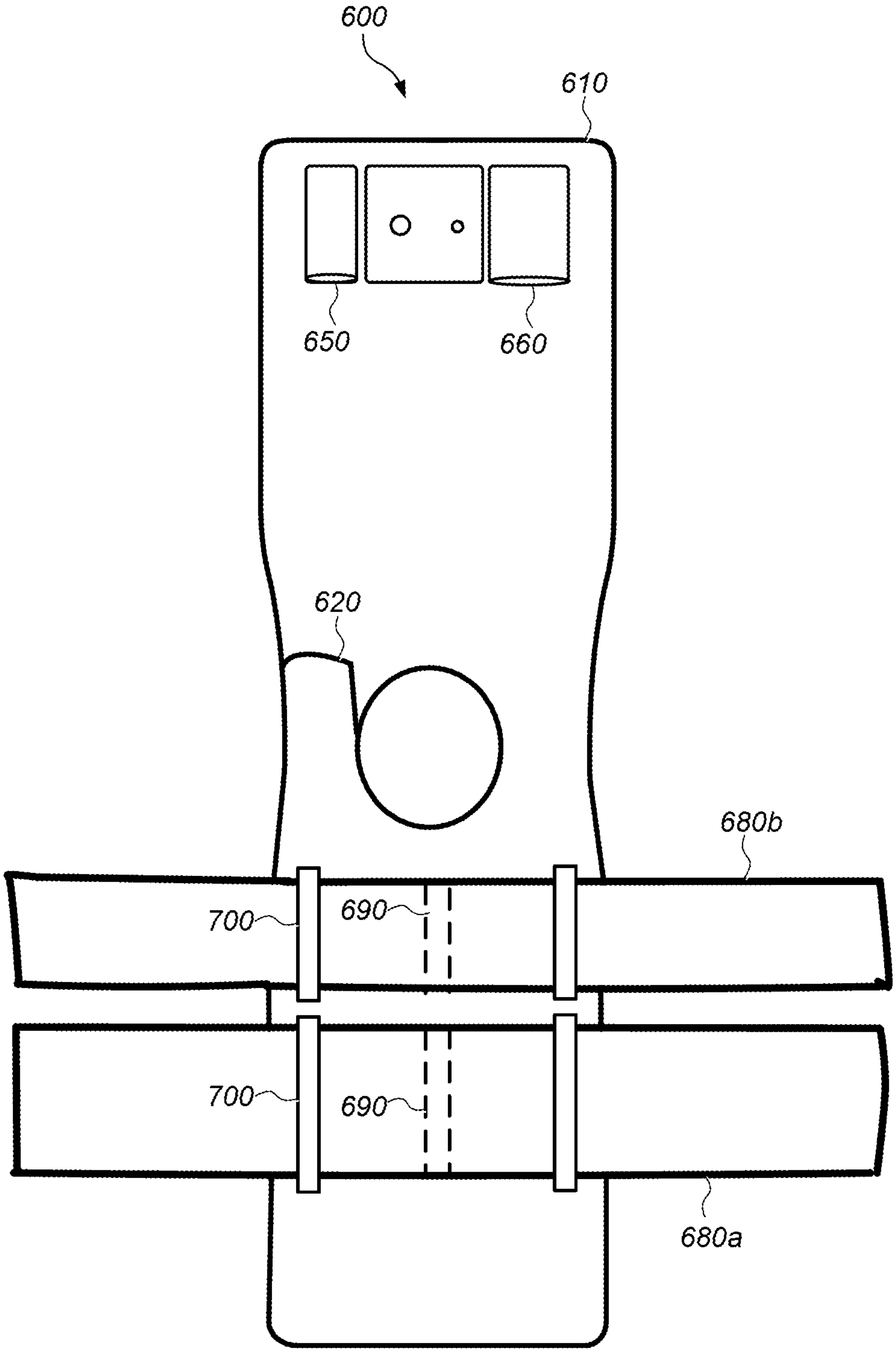
FIG. 26 depicts a front view of a representation of an embodiment of a portable high frequency chest wall oscillator inner harness including secured fasteners as well as two activated outer harnesses positioned on a subject.

In some embodiments, they system 600 may include an outer (or second) harness 680 (e.g., as depicted in FIGS. 14-15 and 20-25). The outer harness 680 may be positionable around at least a portion of an exterior of the inner harness 610. The outer harness may be formed from an elastic, a stretchable or flexible material which when worn compresses or applies pressure or a force or a compressive force to the inner harness and more importantly to any engines beneath the outer harness. Applying pressure to the engines may increase the efficiency of the engines as regards the treatment areas by pressing the engines against the subject. Generally the outer harness may function, during use, to improve transmission of the oscillation force from the engines to the treatment area of the subject. The outer harness may function to further adjust the oscillation force based upon how tightly around the subject the outer harness is secured. The outer harness may function to provide a compressive force based upon how tightly around the subject the outer harness is secured. The outer harness functions to, in some embodiments, gather and/or tighten an inner harness around a subject to provide at least a better fit. In some embodiments, a system may include a single outer wearable harness (e.g., as depicted in FIGS. 20-21). In some embodiments, a system may include two or more outer wearable harnesses (e.g., as depicted in FIGS. 22-25). In some embodiments, a system may include two or more outer wearable harnesses wherein the outer wearable harnesses 680*a*-*b* are different widths (e.g., as depicted in FIG. 26).

The outer harness may allow for fewer sizes of the inner harness to be made available as the outer harness functions to tighten the engines against the subject such that the inner harness does not need to fit as snuggly. A first end of the outer harness may couple to a second end of the outer harness and/or to another portion of the outer harness during use (e.g., using hook and loop, buckles, clasps, etc.). At least a portion of the outer harness may be coupled or directly attached (e.g., permanently fixed (either directly (e.g., sewn to) or indirectly) or temporarily fixed (either directly (e.g., sewn to 690 as depicted in FIG. 25) or indirectly)) to the inner harness. At least a portion of the outer harness may be coupled or directly attached to the inner harness in such a way as to allow movement in one or more directions of the outer harness relative to the inner harness (e.g., a double slit cut into the inner wearable harness through which the outer wearable harness is threaded through allowing latitudinal and/or longitudinal movement). In some embodiments, one or more portions of the outer wearable harness may be coupled or directly attached to the inner wearable harness using elongated members or loops 700 allowing the outer wearable harness to move relative to the inner harness while remaining coupled or directly attached to the inner wearable harness. The loops may allow a subject to more easily access the outer wearable harnesses during use (allowing the subject to more easily reach the outer wearable harnesses).

In some embodiments, the outer harness may include any way of providing a compressive force to against one or more of the engines increasing the efficiency of the oscillating force applied to the subject during use (e.g., an outer harness which laces up, tightening buckles, etc.). This is in contrast to some currently known vests which are rigid, wherein the rigidity of the vest controls the placement of the engines during use.

In some embodiments, one or more engines or portions of the system may be positioned (e.g., coupled or directly attached to) the outer harness (e.g., to an inner and/or outer surface of the outer harness).

Figure 18A:
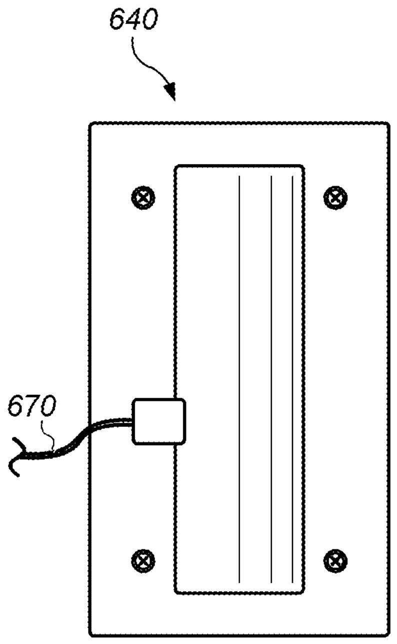
FIGS. 18A-B depict a first and a second opposing side view of a representation of a first embodiment of an engine.
Figure 18B:
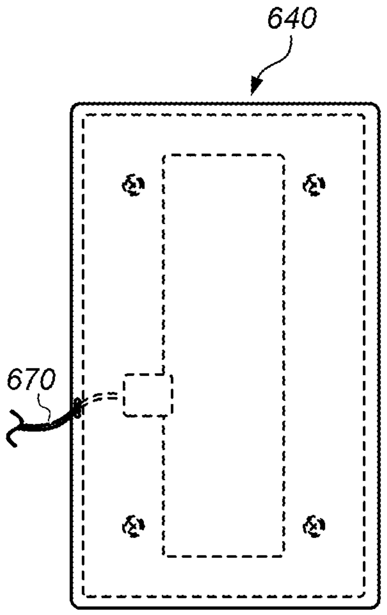
Figure 19:
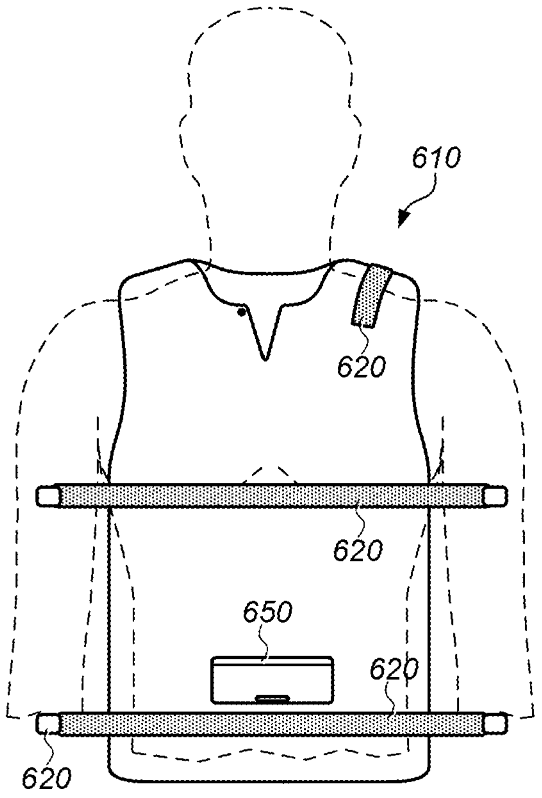
FIG. 19 depicts a front view of a representation of an embodiment of a portable high frequency chest wall oscillator inner harness including unsecured fasteners positioned on a subject.
Figure 18C:
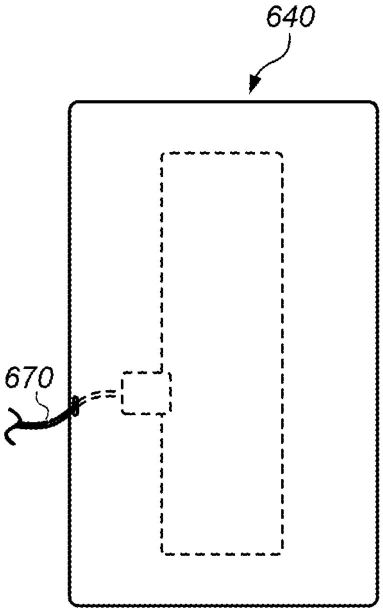
FIG. 18C depicts a side view of a representation of a second embodiment of an engine.

In some embodiments, the wearable system 600 may include multiple engines 640 (e.g., two or more engines, for example, as depicted in FIG. 10). The system may include at least four engines 640, at least six engines 640, at least eight engines 640 or as many engines as necessary (e.g., as prescribed by a physician). In some embodiments, an engine 640 (e.g., as depicted in FIGS. 18A-B) may include electric motors, sonic wave generators, electro-mechanic or electrodynamic vibrators, solenoid, etc. In some embodiments, engines 640 may be positioned in containers 645 (e.g., as depicted in FIG. 24). Containers 645 may be formed from primarily flexible or pliable materials. The container may include fixation means (e.g., hook and loop) which allow for positioning the engines 640 as necessary relative to system 600. The containers may substantially contain the engines 640 using a zipper and/or a closure flap with a button or hook and loop. In some embodiments, one or more containers may include padding (e.g., or be formed from a thicker pliable material). Padded containers may diffuse the oscillation force (e.g., vibration force) over a broader area of a subject, for example, to protect a subject from unintentional injury. The containers may be disposable, for example, for the purpose of controlling infection (e.g., after use discard the containers and reuse the engines. Containers may also be used for batteries and/or controllers. In some embodiments, engines, controllers, and/or batteries may be saved for reuse and/or recycling. In some embodiments, an engine 640 (e.g., as depicted in FIG. 18C) may include a substantially smooth outer covering such that the engine is easier disinfect the engine before and/or after use.

In some embodiments, the system 600 may include a control unit 650 (e.g., as depicted in FIGS. 11, 16, 19-23, and 25). The method may include activating at least the first engine using the control unit 650. The control unit may control activation/deactivation/adjustment of all of the engines of the system 100. In some embodiments, the control unit 650 may be couplable to the inner harness 610 (e.g., using a hook and loop strip 630 as depicted in FIG. 11 or positioned in a pocket as depicted in FIG. 25). The control unit 650 may be directly wired to the engines 640 and/or may be wirelessly coupled or directly attached to the engines. The control unit may use any number of known input methods (e.g., including touchpad). The control unit may be digital or analog. In some embodiments, the control unit may adjust one or more settings of the engines. The control unit may adjust the oscillation force output by the engine. The control unit may adjust an amplitude of the oscillation force output by the engine. The control unit may adjust a frequency of the oscillation force output by the engine. In some embodiments, engine parameters may be adjusted via software (e.g., a phone app) remotely (e.g., Wi-Fi, Bluetooth, etc.).

In some embodiments, the engines 110 may include a frequency range from 5 Hz to 20 Hz. In some embodiments, the intensity levels dictate the frequency which generally runs at 5 Hz for the lowest setting, 13 Hz for the medium setting and 20 Hz for the highest setting. In some embodiments, engines may be grouped together such that frequencies produced by the grouped engines result in a superposition of the produced frequencies in order to achieve frequencies and/or intensities not achievable under normal operating parameters of the engines. For example a superpulse may be achievable, lower frequencies may be achievable. The ability to produce such a variety of different frequencies is beneficial for treating different types of lung disorders. The principle of superposition may be applied to waves whenever two (or more) waves travel through the same medium at the same time. The waves pass through each other without being disturbed. The net displacement of the medium at any point in space or time, is simply the sum of the individual wave displacements. This is true of waves pulses or continuous sine waves. For example, two sinusoidal waves with the same amplitude and frequency can add either destructively or constructively depending on their relative phase. The phase difference between the two waves may increase with time so that the effects of both constructive and destructive interference may be seen. When the two individual waves are exactly in phase the result is large amplitude. When the two waves become exactly out of phase the sum wave is zero.

For example, bronchiectasis is a condition in which damage to the airways causes them to widen and become flabby and scarred preventing the airways from clearing mucus (mucus which is typically voluminous and relatively thin). In contrast cystic fibrosis is a genetic disorder that results in at least difficulty breathing and an inability to clear the lungs of mucus (mucus which is typically relatively thick). Different conditions result in different mucus and/or debris in a subject's lungs which may benefit from different frequencies which may be prescribed by, for example, a physician.

In some embodiments, a method may include modifying the treatment parameters (e.g. amplitude, frequency, and time for each engine). Each engine may be programmed, using physical hardware control unit or software to run a custom cycle. This programming may be performed according to each subject. In addition, the system may provide a physician or caregiver with the ability to prescribe a defined treatment and/or to inhibit the user from modifying the treatment settings (e.g. lock-out feature w/password, pin code, etc.). Each of the motors may be individually programmable (e.g., length of run time, type of vibration (e.g., constant, pulsing, etc.), frequency, amplitude, etc.).

In some embodiments, the method and/or system may adaptively modify the treatment protocol based on subject and/or physician feedback. For example, a subject enters mucus secretion levels after each treatment and the system adaptively optimizes the treatment settings over time.

In some embodiments, the method and/or system may monitor compliance information. For example, the system could monitor (in real-time) the treatment for each subject, including parameters run, time of treatment, time of day and any subject feedback. This could be accomplished through hardware or software (e.g. a web-based subject/physician portal which links w/Bluetooth to each vest). The information may be provided to the subject, physician, insurance company or other third-party.

In some embodiments, the system 600 may include at least one battery 660. The method may include powering the engines 640 using one or more batteries 660 coupled or directly attached to the inner harness of the wearable system. In some embodiments, a battery 660 may include a rechargeable battery and/or a disposable battery. The battery 660 may include two or more batteries. The batteries 660 may be easily swapped out whether rechargeable or disposable. The battery 660 may be coupled or directly attached to the system 600 (e.g., using a hook and loop strip 630 as depicted in FIG. 11). The system may include an adapter such that when necessary the system may be coupled or directly attached to an electrical outlet (e.g., through an electrical adapter if necessary). The system 100 may be powered using AC or DC power sources such that the system may be powered using virtually any known power source currently available.

In some embodiments, the system 600 may include a system of electrical couplings 670. Electrical couplings 670 may couple control unit 650 and/or battery 660 to engines 640 (e.g., as depicted in FIGS. 10-13). The electrical couplings may run on an exterior surface of the inner harness (e.g., as depicted in FIGS. 10-11). The electrical couplings may run under a second layer 610*a* of inner harness 610 (e.g., as depicted in FIGS. 12-13) with coupling ends extending out of openings in the second layer 610*a*. In some embodiments, at least some portions of the electrical couplings may be bound or bundled together (e.g., such that the electrical couplings are easier to separate from the rest of the system 600 for disposal or recycling. In some embodiments, the electrical couplings (e.g., wires) may be sewn in to the disposable inner wearable system. The inner wearable system may include conduits 675 (e.g., fabric, impervious materials (e.g., plastics) as depicted in FIG. 24) for wires coupled or directly attached to and/or sewn into the inner wearable system (e.g., to electrically connect a battery and/or a controller to at least one of the plurality of engines). In some embodiments, conduits 675 may be positionable relative to the inner wearable system. The conduits may be connected to the inner wearable system using hook and loop systems. The wires may provide multiple connection points for the plurality of engines so that the plurality of engines are repositionable while still using the wires in the fabric conduits.

In some embodiments, the system may be self-contained. The system may be self-contained such that a subject may wear the system 600 and move freely and in a substantially unrestricted manner. The system may be self-contained such that a subject may wear the system 600 while functioning and not physically connected to any external devices (e.g., air pumps).

In some embodiments, all, substantially all, or at least one portion of the system 600 may be disposable or recyclable. Making portions of the system 600 disposable may be disposable due to, for example, that much of the equipment used in healthcare environments which comes into direct contact with subjects is disposable (or covered by disposable sheaths). It is typically much easier and/or less expensive to throw away equipment which comes into contact with subjects as opposed to cleaning the equipment. In some embodiments, the inner wearable harness is disposable. In some embodiments, the outer wearable harness is disposable. In some embodiments, at least some of the plurality of engines are disposable. In some embodiments, the inner and/or outer harness and the engines may be disposable.

In some embodiments, one or more portions of the system 600 are recyclable. For example self-contained portions of the system (e.g., engines 640) may be recyclable in order to reduce waste.

In some embodiments, one or more portions of the systems describe herein may include antimicrobial coatings (e.g, in fabrics of the vests). In some embodiments, one or more portions of the systems described herein may be able to withstand one or more common medical sterilization techniques (e.g., high temperature, high pressure, chemical, etc.). In some embodiments, one or more portions (e.g, in fabrics of the vests or the containers for one or more engines) may include an impervious materials, coatings, or linings such that one or more portions of the system are protected from or at least inhibited from exposure to one or more contaminants. For example, a lining or material may be substantially impervious to water or blood borne pathogens or contaminants. For example, a lining or material may be substantially impervious to gasses and/or air borne pathogens or contaminants. In some embodiments, a container such as a positionable engine container 645 may include an impervious or impermeable lining which inhibits contamination of an engine positioned in the container such that the engine may be more easily recycled.

In this patent, certain U.S. patents, U.S. patent applications, and other materials (e.g., articles) have been incorporated by reference. The text of such U.S. patents, U.S. patent applications, and other materials is, however, only incorporated by reference to the extent that no conflict exists between such text and the other statements and drawings set forth herein. In the event of such conflict, then any such conflicting text in such incorporated by reference U.S. patents, U.S. patent applications, and other materials is specifically not incorporated by reference in this patent.

Further modifications and alternative embodiments of various aspects of the invention will be apparent to those skilled in the art in view of this description. Accordingly, this description is to be construed as illustrative only and is for the purpose of teaching those skilled in the art the general manner of carrying out the invention. It is to be understood that the forms of the invention shown and described herein are to be taken as the presently preferred embodiments. Elements and materials may be substituted for those illustrated and described herein, parts and processes may be reversed, and certain features of the invention may be utilized independently, all as would be apparent to one skilled in the art after having the benefit of this description of the invention. Changes may be made in the elements described herein without departing from the spirit and scope of the invention as described in the following claims.

What is claimed is:

1. A method of clearing a biological airway, comprising:
- positioning a first wearable harness on a torso of a subject;
- positioning a second wearable harness on a torso of a subject over at least a portion of an outer surface of the first wearable harness;
- selectively positioning at least some of a plurality of engines on and/or adjacent at least one treatment area, wherein at least one of the plurality of engines is releasably couplable to the first wearable harness or the second wearable harness such that the at least one of the plurality of engines is positionable relative to the subject using a positioning system, wherein each of the one or more of the plurality of engines applying oscillation force is individually programmed according to the set of treatment parameters;
- mobilizing at least some secretions in an airway within the subject substantially adjacent one or more treatment areas for a first treatment period, wherein mobilizing the at least some secretions for the first treatment period includes:
  - applying an oscillation force to the one or more treatment areas using one or more of the plurality of engines, wherein each of the one or more engines applying the oscillation force is programmed according to a set of treatment parameters, the set of treatment parameters including properties for operation of the engines during treatment;
  - adjusting the oscillation force applied by at least some of the activated plurality of engines to the treatment area by activating the second wearable harness;
- modifying at least one treatment parameter in the set of treatment parameters following the first treatment period, wherein the at least one treatment parameter is modified based on a mucus secretion level of the subject after the first treatment period, and
- mobilizing at least some secretions in the airway within the subject substantially adjacent the one or more treatment areas for a second treatment period, wherein mobilizing the at least some secretions for the first treatment period includes:
  - applying the oscillation force to the one or more treatment areas using the one or more of the plurality of engines, wherein at least one of the engines applying the oscillation force is programmed according to the modified at least one treatment parameter.

2. The method of claim 1, wherein adjusting the oscillation force comprises providing a compressive force to at least one of the plurality of engines using the second wearable harness.

3. The method of claim 1, further comprising assessing treatment areas of the subject's chest for selective placement of at least some of the plurality of the engines, such that the at least some of the plurality of engines are adjacent treatment areas that need secretion mobilization.

4. The method of claim 1, further comprising assessing treatment areas of the subject's chest for selective placement of at least some of the plurality of the engines, such that the at least some of the plurality of engines are adjacent treatment areas that need secretion mobilization, wherein assessing treatment areas comprises using MRI and/or X-ray.

5. The method of claim 1, further comprising assessing treatment areas of the subject's chest for selective placement of at least some of the plurality of the engines, such that the at least some of the plurality of engines are adjacent treatment areas that need secretion mobilization, wherein assessing treatment areas comprises assessing where to reposition the at least some of the plurality of engines after data is gathered after the initial placement.

6. The method of claim 1, further comprising adjusting a fit of the first wearable harness to the subject's torso using the second wearable harness.

7. The method of claim 1, wherein at least a majority of the first wearable harness is formed from a flexible material.

8. The method of claim 1, wherein the second wearable harness comprises a flexible material.

9. The method of claim 1, wherein the positioning system used to releasably couple at least some of the plurality of engines to the first wearable harness or the second wearable harness using a hook and loop system.

10. The method of claim 1, further comprising adjusting an amplitude of the oscillation force using a controller.

11. The method of claim 1, further comprising adjusting a frequency of the oscillation force using a controller.

12. The method of claim 1, further comprising activating the plurality of engines using a control unit.

13. The method of claim 1, further comprising powering the plurality of engines using one or more batteries coupled to the first or second wearable harness.

14. The method of claim 1, further comprising inhibiting removal of the first wearable harness from the subject, during use, using a fastening system.

15. The method of claim 1, further comprising:
- inhibiting removal of the first wearable harness from the subject, during use, using a fastening system; and
- adjusting a fit of the first wearable harness to the subject at least in part using the fastening system.

16. The method of claim 1, wherein the first wearable harness is a vest comprising an opening for a head of the subject, and openings for arms of the subject.

17. The method of claim 1, wherein the first wearable harness is a vest comprising an opening for a head of the subject, and openings for arms of the subject, and further comprising positioning at least four engines, after the vest has been positioned on the subject, on different areas of the vest to allow selective placement of engines adjacent areas of the subject's chest.

18. The method of claim 1, wherein the positioning system comprises a plurality of sealable containers.

19. The method of claim 1, wherein the second wearable harness comprises at least one stretchable band, and wherein a first portion of the second wearable harness is couplable to a second portion of the second wearable harness.

20. The method of claim 1, wherein the second wearable harness comprises at least one stretchable band coupled to the first wearable harness, and wherein a first portion of the second wearable harness is couplable to a second portion of the second wearable harness.

21. The method of claim 1, wherein the positioning system comprises a plurality of pockets integrally formed in the first wearable harness or the second wearable harness such that at least one of the plurality of engines is positionable in one of the plurality of pockets formed in the first wearable harness, wherein the plurality of pockets comprises at least sixteen pockets, and wherein selectively positioning at least some of a plurality of engines comprises leaving some of the plurality of pockets empty nonadjacent to the at least one treatment area.

22. The method of claim 1, wherein the properties for operation of the engines during treatment include one or more of the following properties: amplitude of oscillation force, frequency of oscillation force, time for engine operation, and type of engine vibration.

* * * * *